US011045465B2

(12) United States Patent
Bhide et al.

(10) Patent No.: US 11,045,465 B2
(45) Date of Patent: Jun. 29, 2021

(54) METHODS AND COMPOSITIONS TO PREVENT ADDICTION

(71) Applicants: FLORIDA STATE UNIVERSITY RESEARCH FOUNDATION, INC., Tallahassee, FL (US); THE GENERAL HOSPITAL CORPORATION, Boston, MA (US)

(72) Inventors: Pradeep G. Bhide, Peabody, MA (US); Jinmin Zhu, Allston, MA (US); Thomas J. Spencer, Carlisle, MA (US); Joseph Biederman, Brookline, MA (US)

(73) Assignees: Florida State University Research Foundation, Inc., Tallahassee, FL (US); General Hospital Corporation, Boston, MA (US)

( * ) Notice: Subject to any disclaimer, the term of this patent is extended or adjusted under 35 U.S.C. 154(b) by 188 days.

(21) Appl. No.: 13/924,815

(22) Filed: Jun. 24, 2013

(65) Prior Publication Data
US 2013/0289061 A1   Oct. 31, 2013

Related U.S. Application Data

(63) Continuation of application No. 13/389,959, filed as application No. PCT/US2010/045486 on Aug. 13, 2010, now abandoned.

(60) Provisional application No. 61/233,686, filed on Aug. 13, 2009.

(51) Int. Cl.
| | |
|---|---|
| A61K 31/485 | (2006.01) |
| A61K 31/135 | (2006.01) |
| A61K 45/06 | (2006.01) |
| A61K 31/44 | (2006.01) |
| A61K 31/4458 | (2006.01) |

(52) U.S. Cl.
CPC .......... *A61K 31/485* (2013.01); *A61K 31/135* (2013.01); *A61K 31/44* (2013.01); *A61K 31/4458* (2013.01); *A61K 45/06* (2013.01)

(58) Field of Classification Search
CPC combination set(s) only.
See application file for complete search history.

(56) References Cited

U.S. PATENT DOCUMENTS

| | | | |
|---|---|---|---|
| 6,528,518 B2 | 3/2003 | Carlezon | |
| 6,638,533 B2 * | 10/2003 | Krsek ................... | A61K 9/2081 424/405 |
| 2005/0063909 A1 | 3/2005 | Wright et al. | |
| 2005/0214223 A1 | 9/2005 | Bartholomaeus et al. | |
| 2009/0175939 A1 | 7/2009 | Bosse et al. | |
| 2010/0168119 A1 | 7/2010 | Bear et al. | |

FOREIGN PATENT DOCUMENTS

| | | |
|---|---|---|
| WO | 2004/091546 A2 | 10/2004 |
| WO | 2007/0120864 A2 | 10/2007 |

OTHER PUBLICATIONS

Monafinil (Statewide Pharmacy and Therapeutics Committee Formulary Review for Mondafinil, Jun. 14, 2002, http://www.pharmacy.umaryland.edu/programs/mhaformulary/formulary%20reviews/pdfs/2002/modafinil.pdf, pp. 1-5).*
Boyles (Narcolepsy Drug show Promise for ADHD, 2005, https://www.webmd.com/add-adhd/childhood-adhd/news/20051206/narcolepsy-drug-sho . . . Oct. 26, 2017 WebMD does not provide medical advice, diagnosis or treatment.Narcolepsy Drug Shows Promise for ADHD).*
Jayaram-Lindstrom (Naltrexone for the Treatment of Amphetamine Dependence: A Randomized, Placebo-Controlled Trial, Am J Psychiatry 2008; 165:1442-1448).*
O'Brien (Evidence-based treatments of addiction, Phil. Trans. R. Soc. B (2008) 363, 3277-3286).*
Halladay (Methylphenidate potentiates morphine-induced antinociception, hyperthermia, and locomotor activity in young adult rats, Pharmacol Biochem Behav. Mar. 2009 ; 92(1): 190-196).*
Pierce (vol. C, Module 2 Opiods: Basics of Addiction: Treatment with Agonist, Partial Agonist, and Antagonist and update, United Nations Office on Drugs and Crime, Feb. 2000, pp. 1-188).*
Chi-Tso (Methamphetamine-induced behavioral sensitization in mice: alterations in μ-opioid receptor, J Biomed Sci. Nov. 2006 ; 13(6): 797-811 (renumbered pp. 1-22)).*
Goodwin (Amphetamine and Methamphetamine Differentially Affect Dopamine Transporters in Vitro and in Vivo, The Journal of Biological Chemistry vol. 284, No. 5, pp. 2978-2989, Jan. 30, 2009).*
Ren, J. Q. Jiang, Y. et al. "Prenatal L-DOPA exposure produces lasting changes in brain dopamine content, cocaine-induced dopamine release and cocaine conditioned place preference." Neuropharmacology 60(2-3): 295-302 (2011).

(Continued)

Primary Examiner — Kathrien A Cruz
(74) Attorney, Agent, or Firm — Clark & Elbing LLP

(57) ABSTRACT

Disclosed herein is a method of reducing or preventing the development of aversion to a CNS stimulant in a subject comprising, administering a therapeutic amount of the neurological stimulant and administering an antagonist of the kappa opioid receptor, to thereby reduce or prevent the development of aversion to the CNS stimulant in the subject. Also disclosed is a method of reducing or preventing the development of addiction to a CNS stimulant in a subject, comprising, administering the CNS stimulant and administering a mu opioid receptor antagonist to thereby reduce or prevent the development of addiction to the CNS stimulant in the subject. Also disclosed are pharmaceutical compositions comprising a central nervous system stimulant and an opioid receptor antagonist. Examples of central nervous system stimulants (such as methylphenidate) and opioid receptor antagonists (such as naltrexone) are provided.

17 Claims, 12 Drawing Sheets

(56) References Cited

OTHER PUBLICATIONS

Robbins, T. W. "ADHD and addiction." Nat. Med. 8(1): 24-25 (2002).
Russell, V. A., Sagvolden, T., et al. "Animal models of attention-deficit hyperactivity disorder." Behav. Brain Funct. 1: 9 (2005).
Sagvolden, T., Russell, V. A., et al. "Rodent models of attention-deficit/hyperactivity disorder." Biol. Psychiatry 57(11): 1239-47 (2005).
Sagvolden T, Johansen EB, Woien G, Walaas SI, Storm-Mathisen J, Bergersen LH, Hvalby O, Jensen V, Aase H, Russell VA, Killeen PR, Dasbanerjee T, Middleton FA, Faraone SV, "The spontaneously hypertensive rat model of ADHD—the importance of selecting the appropriate reference strain," Neuropharmacology 57:619-626 (2009).
Schneider, T., Ilott, N., et al. "Prenatal exposure to nicotine impairs performance of the 5-choice serial reaction time task in adult rats." Neuropsychopharmacology 36(5): 1114-25 (2011).
Svingos, A. L., Chavkin, C., et al. "Major coexpression of kappa-opioid receptors and the dopamine transporter in nucleus accumbens axonal profiles." Synapse 42(3): 185-92 (2001).
Svingos, A. L., Garzon, M., et al. "Mu-opioid receptors in the ventral tegmental area are targeted to presynaptically and directly modulate mesocortical projection neurons." Synapse 41(3): 221-29 (2001).
Svingos, A. L. and Colago, E. E. "Kappa-Opioid and NMDA glutamate receptors are differentially targeted within rat medial prefrontal cortex." Brain Res. 946(2): 262-71 (2002).
Takemori, A. E., Ho, B. Y., et al. "Nor-binaltorphimine, a highly selective kappa-opioid antagonist in analgesic and receptor binding assays." J. Pharmacol. Exp. Ther. 246(1): 255-58 (1988).
Thompson, A. C., Zapata, A., et al. "Kappa-opioid receptor activation modifies dopamine uptake in the nucleus accumbens and opposes the effects of cocaine." J. Neurosci. 20(24): 9333-40 (2000).
Todtenkopf, M. S., Marcus, J. F., et al. "Effects of kappa-opioid receptor ligands on intracranial self-stimulation in rats." Psychopharmacology (Berl) 172(4): 463-70 (2004).
Varaschin, R. K. and Morato, G. S. "Selective mu- and kappa-opioid receptor antagonists administered into the nucleus accumbens interfere with rapid tolerance to ethanol in rats." Psychopharmacology (Berl) 206(1): 85-96 (2009).
Volkow N.D., Fowler J. S., Gatley SJ, Dewey SL, Wang GJ, Logan J, Ding YS, Franceschi D, Gifford A, Morgan A, Pappas N, King P, "Comparable changes in synaptic dopamine induced by methylphenidate and by cocaine in the baboon brain." Synapse 31:59-66 (1999).
Volkow, N. D., Wang, G. J., et al. "Methylphenidate and cocaine have a similar in vivo potency to block dopamine transporters in the human brain." Life Sci. 65(1): PL7-12 (1999).
Wickstrom, R. "Effects of nicotine during pregnancy: human and experimental evidence." Current neuropharmacology 5(3): 213-22 (2007).
Wiley, M. D., Poveromo, L. B., et al. "Kappa-opioid system regulates the long-lasting behavioral adaptations induced by early-life exposure to methylphenidate." Neuropsychopharmacology 34(5): 1339-50 (2009).
Willemsen-Swinkels, S. H., Buitelaar, J. K., et al. "The effects of chronic naltrexone treatment in young autistic children: a double-blind placebo-controlled crossover study." Biol. Psychiatry 39(12): 1023-31 (1996).
Yano, M. and Steiner, H. "Methylphenidate and cocaine: the same effects on gene regulation?" Trends Pharmacol. Sci .28(11): 588-596 (2007).
You, Z. B., Herrera-Marschitz, M., et al. "Modulation of neurotransmitter release in the basal ganglia of the rat brain by dynorphin peptides." J. Pharmacol. Exp. Ther. 290(3): 1307-15 (1999).
Zagon, I. S. "Endogenous opioids, opioid receptors, and neuronal development." NIDA Res. Monogr. 78: 61-71 (1987).
Zagon, I. S. and McLaughlin, P. J. "Increased brain size and cellular content in infant rats treated with an opiate antagonist." Science 221(4616): 1179-80 (1983).
Zagon, I. S. and McLaughlin, P. J. "Naltrexone modulates growth in infant rats." Life Sci. 33(24): 2449-54 (1983).
Zagon, I. S. and McLaughlin, P. J. "Endogenous opioid systems regulate cell proliferation in the developing rat brain." Brain Res. 412(1): 68-72 (1987).
Zhang, L., Shirayama, Y., et al. "Minocycline attenuates hyperlocomotion and prepulse inhibition deficits in mice after administration of the NMDA receptor antagonist dizocilpine." Neuropsychopharmacology 32(9): 2004-10 (2007).
Zhu, J. M., X. P. He, et al. "Changes of releases of beta-endorphin-like immunoreactive substances and noradrenaline in rabbit's preoptic area during acupuncture analgesia." Sheng Li Xue Bao 42(2): 188-93 (1990) (Abstract Only).
Zhu, J., Chen, C. et al. "Cloning of a human kappa opioid receptor from the brain." Life Sci. 56(9): PL201-07 (1995).
Zhu, J., Xue, J. C., et al. "The region in the mu opioid receptor conferring selectivity for sufentanil over the delta receptor is different from that over the kappa receptor." FEBS Lett. 384(2): 198-202 (1996).
Zhu, J., Zhang, X., et al. "Prenatal nicotine exposure mouse model showing hyperactivity, reduced cingulate cortex volume, reduced dopamine turnover, and responsiveness to oral methylphenidate treatment." J. Neurosci. 32(27): 9410-18 (2012).
Zuvekas, S. H., Vitiello, B., et al. "Recent trends in stimulant medication use among U.S. children." Am. J. Psychiatry 163(4): 579-85 (2006).
Hauser, K. F., McLaughlin, P. J., et al. "Endogenous Opioid Systems and the Regulation of Dendritic Growth and Spine Formation", J. of Comparative Neurology, 281: 13-22 (1989).
Balcioglu, A., Ren, J-Q., McCarthy, D.M., Spencer, T. J., Biederman, J., Bhide, P. G. Plasma and brain concentrations of oral therapeutic doses of methylphenidate and their impact on brain monoamine content in mice. Neuropharmacology 57(7-8):687-93 (2009).
Bergman, J., Madras, B. K., et al. "Effects of cocaine and related drugs in nonhuman primates. III. Self-administration by squirrel monkeys." J. Pharmacol. Exp. Ther. 251(1): 150-55 (1989).
Bhargava, H. N., Gulati A, "Kappa opioid receptor activity in spontaneously hypertensive rats," The Journal of Pharmacology and Experimental Therapeutics 245:460-465 (1988).
Biederman, J., T. Wilens, et al. "Is ADHD a risk factor for psychoactive substance use disorders? Findings from a four-year prospective follow-up study." J. Am. Acad. Child. Adolesc. Psychiatry 36(1): 21-29 (1997).
Biederman, J., Wilens, T. E., et al. "Does attention-deficit hyperactivity disorder impact the developmental course of drug and alcohol abuse and dependence?" Biol. Psychiatry 44(4): 269-73 (1998).
Biederman, J. "Attention-deficit/hyperactivity disorder: a selective overview." Biol Psychiatry 57(11): 1215-20 (2005).
Bolanos, C. A., Garmsen, G. M., et al., "Effects of the kappa-opioid receptor agonist U-50,488 on morphine-induced place preference conditioning in the developing rat." Eur. J. Pharmacol. 317(1): 1-8 (1996).
Bright, G. M. "Abuse of medications employed for the treatment of ADHD: results from a large-scale community survey." Medscape J. Med. 10(5): 111(2008).
Broom, D. C., Jutkiewicz, E. M., et al. "Nonpeptidic delta-opioid receptor agonists reduce immobility in the forced swim assay in rats." Neuropsychopharmacology 26(6): 744-55, (2002).
Brown, R. T., Amler, R. W., et al. "Treatment of attention-deficit/hyperactivity disorder: overview of the evidence." Pediatrics 115(6): e749-57 (2005).
Bryant, C. D., Roberts, K. W., et al. "Pavlovian conditioning of multiple opioid-like responses in mice." Drug Alcohol Depend. 103(1-2): 74-83 (2009).
Campbell, M., Anderson, L. T., et al. "Naltrexone in autistic children: behavioral symptoms and attentional learning." J. Am. Acad. Child Adolesc. Psychiatry 32(6): 1283-91 (1993).
Carlezon, W. A., Jr., Beguin, C., et al. "Depressive-like effects of the kappa-opioid receptor agonist salvinorin A on behavior and neurochemistry in rats." J. Pharmacol. Exp. Ther. 316(1): 440-47 (2006).

(56) References Cited

OTHER PUBLICATIONS

Chefer, V. I., Moron, J. A., et al. "Kappa-opioid receptor activation prevents alterations in mesocortical dopamine neurotransmission that occur during abstinence from cocaine." Neuroscience 101(3): 619-27 (2000).
Cummings, J. L. "Frontal-subcortical circuits and human behavior." Arch. Neurol. 50(8): 873-80 (1993).
Dean, R. L., Todtenkopf, M. S. et al. "Overriding the blockade of antinociceptive actions of opioids in rats treated with extended-release naltrexone." Pharmacol. Biochem. Behav. 89(4): 515-22 (2008).
Di Chiara, G. and Imperato, A. "Drugs abused by humans preferentially increase synaptic dopamine concentrations in the mesolimbic system of freely moving rats." Proc. Natl. Acad. Sci. USA 85(14): 5274-78 (1988).
Donahue, R. N., McLaughlin, P. J., et al. "Low-dose naltrexone targets the opioid growth factor-opioid growth factor receptor pathway to inhibit cell proliferation: mechanistic evidence from a tissue culture model." Exp. Biol. Med. (Maywood) 236(9): 1036-50 (2011).
Drake, C. T., Patterson, T. A., et al. "Kappa opioid receptor-like immunoreactivity in guinea pig brain: ultrastructural localization in presynaptic terminals in hippocampal formation." J. Comp. Neurol. 370(3): 377-95 (1996).
Elchaar, G. M., Maisch, N. M., et al. "Efficacy and safety of naltrexone use in pediatric patients with autistic disorder." Ann. Pharmacother. 40(6): 1086-95 (2006).
Endoh, T., Matsuura, H., et al. "Nor-binaltorphimine: a potent and selective kappa-opioid receptor antagonist with long-lasting activity in vivo." Arch. Int. Pharmacodyn. Ther. 316: 30-42 (1992) (Abstract Only).
Evans, C. J.,. Keith, D. E.,Jr., et al. "Cloning of a delta opioid receptor by functional expression." Science 258(5090): 1952-55 (1992).
Feldman, H. M., Kolmen, B. K., et al. "Naltrexone and communication skills in young children with autism." J. Am. Acad. Child Adolesc. Psychiatry 38(5): 587-93 (1999).
Gerasimov, A. A. and Volkova, A. M. "[Treatment of patients with lumbar osteochondrosis by the method of intra-tissular electric stimulation]." Ortop. Travmatol. Protez. (5): 13-17 (1991) (Abstract Only).
Hauser, K. F., McLaughlin, P. J., et al. "Endogenous opioids regulate dendritic growth and spine formation in developing rat brain." Brain Res. 416(1): 157-61 (1987).
Hellman, K. M., Mendelson, S. J., et al. "Opioid microinjection into raphe magnus modulates cardiorespiratory function in mice and rats." Am. J. Physiol. Regul. Integr. Comp. Physiol. 297(5): R1400-08 (2009).
Huizink, A. C. and Mulder, E. J. "Maternal smoking, drinking or cannabis use during pregnancy and neurobehavioral and cognitive functioning in human offspring." Neurosci. Biobehav. Rev. 30(1): 24-41 (2006).
Jomary, C., Gairin, J. E., et al. "Synaptic localization of kappa opioid receptors in guinea pig neostriatum." Proc. Natl. Acad. Sci. USA 89(2): 564-68 (1992).
Jones, D. N. and Holtzman, S. G. "Long term kappa-opioid receptor blockade following nor-binaltorphimine." Eur. J. Pharmacol. 215(2-3): 345-48 (1992).
Kieffer, B.L., Befort, K., et al. "The delta-opioid receptor: isolation of a cDNA by expression cloning and pharmacological characterization." Proc. Natl. Acad. Sci. USA 89(24): 12048-52 (1992).
Klein-Schwartz, W. "Abuse and toxicity of methylphenidate." Curr. Opin. Pediatr. 14(2): 219-23 (2002).
Knoll, A. T., Meloni, E. G., et al. "Anxiolytic-like effects of kappa-opioid receptor antagonists in models of unlearned and learned fear in rats." J. Pharmacol. Exp. Ther. 323(3): 838-45 (2007).
Kuczenski, R. and Segal, D. S. "Exposure of adolescent rats to oral methylphenidate: preferential effects on extracellular norepineph-rine and absence of sensitization and cross-sensitization to methamphetamine." J. Neurosci. 22(16): 7264-71 (2002).
Kuczenski, R. and Segal, D. S. "Stimulant actions in rodents: implications for attention-deficit/hyperactivity disorder treatment and potential substance abuse." Biol. Psychiatry 57(11): 1391-96 (2005).
Li, S., Zhu, J., et al. "Molecular cloning and expression of a rat kappa opioid receptor." Biochem. J. 295 ( Pt 3): 629-33 (1993).
Linnet, K. M., Dalsgaard, S., et al. "Maternal lifestyle factors in pregnancy risk of attention deficit hyperactivity disorder and associated behaviors: review of the current evidence." Am. J. Psychiatry 160(6): 1028-40 (2003).
Mahler, S. V. and K. C. Berridge, "What and when to "want"? Amygdala-based focusing of incentive salience upon sugar and sex." Psychopharmacology (Berl) 221(3): 407-426 (2012).
Maisonneuve, I. M., Archer, S., et al. "U50,488, a kappa opioid receptor agonist, attenuates cocaine-induced increases in extracellular dopamine in the nucleus accumbens of rats." Neurosci. Lett. 181(1-2): 57-60 (1994) (Abstract Only).
Margolis, E. B., Lock, H., et al. "Kappa opioids selectively control dopaminergic neurons projecting to the prefrontal cortex." Proc. Natl. Acad. Sci. USA 103(8): 2938-42 (2006).
McLaughlin, P. J., Sassani, J. W., et al. "Diabetic keratopathy and treatment by modulation of the opioid growth factor (OGF)-OGF receptor (OGFr) axis with naltrexone: a review." Brain Res. Bull. 81(2-3): 236-47 (2010).
Meshul, C. K. and McGinty, J. F. "Kappa opioid receptor immunoreactivity in the nucleus accumbens and caudate-putamen is primarily associated with synaptic vesicles in axons." Neuroscience 96(1): 91-99 (2000).
Metcalf MD, Coop A, "Kappa opioid antagonists: past successes and future prospects," The AAPS journal 7:E704-722 (2005).
Milberger, S., Biederman, J., et al. "Is maternal smoking during pregnancy a risk factor for attention deficit hyperactivity disorder in children?" Am. J. Psychiatry 153(9): 1138-42 (1996).
Mill, J. "Rodent models: Utility for candidate gene studies in human attention-deficit hyperactivity disorder (ADHD)." J. Neurosci. Methods 166(2):294-305 (2007).
Olfson, M., Marcus, S. C., et al. "National trends in the use of psychotropic medications by children." J. Am. Acad. Child. Adoles.c Psychiatry 41(5): 514-21 (2002).
Patrick, K. S. and Markowitz, J. S. "Pharmacology of methylphenidate, amphetamine enantiomers and pemoline in attention-deficit hyperactivity disorder." Human Psychopharmacol. 12(6): 527-46 (1997).
Patkar, K. A., Wu, J., Ganno, M. L., Singh, H. D., Ross, N. C., Rasakham, K., Toll, L., McLaughlin, J. P., "Physical Presence of Nor-Binaltorphimine in Mouse Brain over 21 Days after a Single Administration Corresponds to Its Long-Lasting Antagonistic Effect on kappa-Opioid Receptors," The Journal of pharmacology and experimental therapeutics 346:545-554 (2013).
Pauly, J. R. and Slotkin, T. A. "Maternal tobacco smoking, nicotine replacement and neurobehavioural development." Acta Paediatr. 97(10): 1331-37 (2008).
Randall-Thompson, J. F., Pescatore, K. A., et al. "A role for delta opioid receptors in the central nucleus of the amygdala in anxiety-like behaviors." Psychopharmacology (Berl) 212(4): 585-95 (2010).
Recant, L., Voyles, N. R., et al. "Naltrexone reduces weight gain, alters "beta-endorphin", and reduces insulin output from pancreatic islets of genetically obese mice." Peptides 1(4): 309-13 (1980) (Abstract Only).
Jayaram-Lindstrom et al., "Effects of Naltrexone on the Subjective Response to Amphetamine in Healthy Volunteers," J Clin Psychopharmacol, 24(6):665-669 (2004).
Kuczenski et al., "Locomotor effects of acute and repeated threshold doses of amphetamine and methylphenidate: relative roles of dopamine and norepinephrine," J Pharmacol Exp Ther, 296(3): 876-883 (2001).
Madras et al., "Effects of cocaine and related drugs in nonhuman primates. I. [3H]cocaine binding sites in caudate-putamen," J Pharmacol Exp Ther, 251(1):131-141 (1989).
Maldonado et al., "Absence of opiate rewarding effects in mice lacking dopamine D2 receptors," Nature, 388:586-589 (1997).

(56) References Cited

OTHER PUBLICATIONS

Meririnne et al., "Rewarding properties of methylphenidate: sensitization by prior exposure to the drug and effects of dopamine D1- and D2-receptor antagonists," J Pharmacol Exp Ther 298(2): 539-550 (2001).
Seeman et al., "Methylphenidate elevates resting dopamine which lowers the impulse-triggered release of dopamine: a hypothesis," Behav Brain Res, 130:79-83 (2002).
Soderman et al., "Cocaine reward and hyperactivity in the rat: sites of mu opioid receptor modulation," Neuroscience, 154:1506-1516, (2008).
Sora et al., "Cocaine reward models: Conditioned place preference can be established in dopamine- and in serotonin-transporter knockout mice," Proc. Nat. Acad. Sci., 95(13):7699-7704, (1998).
Spencer et al., "PET study examining pharmacokinetics, detection and likeability, and dopamine transporter receptor occupancy of short- and long-acting oral methylphenidate," Am J Psychiatry, 163(3):387-395, (2006).
Tien et al., "Increased dopamine D2 receptor binding and enhanced apomorphine-induced locomotor activity in [mu]-opioid receptor knockout mice," Brain Research Bulletin, 61:109-115, (2003).
Trigo et al., "The endogenous opioid system: A common substrate in drug addiction," Drug Alcohol Depend, 108(3):183-194, (2010).
Volkow, "Stimulant medications: how to minimize their reinforcing effects?," Am J Psychiatry, 163(3):359-361, (2006).
Volkow et al., "Imaging the effects of methylphenidate on brain dopamine: new model on its therapeutic actions for attention-deficit/hyperactivity disorder," Biol Psychiatry 57, 1410-1415, (2005).
Xia et al., "Acute Amphetamine Exposure Selectively Desensitizes [kappa]-Opioid Receptors in the Nucleus Accumbens," Neuropsychopharmacology, 33(4):892-900, (2008).
Zhu et al., "Methylphenidate and μ opioid receptor interactions: A pharmacological target for prevention of stimulant abuse," Neuropharmacology, 61(1-2): 283-292 (2011).
Zhu et al., "Activation of the cloned human kappa opioid receptor by agonists enhances [35S]GTPgammaS binding to membranes: determination of potencies and efficacies of ligands," J Pharrnacol Exp Ther, 282(2):676-684, (1997).
Zubieta et al. Increased mu opioid receptor binding detected by PET in cocaine-dependent men is associated with cocaine craving, Nat Med, 2(11):1225-1229, (1996).
Biederman et al., "Attention-deficit hyperactivity disorder," Lancet. 366(9481):237-48 (2005).
Biederman, "Advances in the neurobiology of ADHD," CNS Spectr. 12(4 Suppl 6): 6-7 (2007) (6 pages).
Faraone et al., "Attention-deficit/hyperactivity disorder," Nat Rev Dis Primers. 1:15020 (2015) (23 pages).
Faraone et al., "Attention-Deficit/Hyperactivity Disorder in Adults: An Overview," Biol Psychiatry. 48(1):9-20 (2000).
Faraone et al., "ADHD: disorder or discipline problem?" Science. 291(5508): 1488-1489 (2001) (3 pages).
Spencer et al., "Attention-Deficit/Hyperactivity Disorder: Diagnosis, Lifespan, Comorbidities, and Neurobiology," J Pediatr Psychol. 32(6):631-642 (2007).
Spencer et al., "Opiate Antagonists Do Not Interfere with the Clinical Benefits of Stimulants in ADHD: A Double-Blind, Placebo-Controlled Trial of the Mixed Opioid Receptor Antagonist Naltrexone," J. Clin. Psychiatry. e1-e7 (2017) (7 pages).
Swanson et al., "Activating Tasks for the Study of Visual-Spatial Attention in ADHD Children: A Cognitive Anatomic Approach," J Child Neurol. 6 Suppl: S119-27 (1991) (2 pages) (Abstract Only).
Wender et al., "Adults with ADHD. An Overview," Ann N Y Acad Sci. 931: 1-16 (2001).
Dhawan et al., "International Union of Pharmacology. XII. Classification of Opioid Receptors," Pharmacol Rev. 48(4): 567-592 (1996).
Jayaram-Lindström et al., "An open clinical trial of naltrexone for amphetamine dependence: Compliance and tolerability," Nord J Psychiatry. 59(3):167-171 (2005).
Schmidhammer, "Opioid Receptor Anatagonists," Prog Med Chem. 35:83-132 (1998).
Biederman et al., "Attention-deficit/hyperactivity disorder (adhd) as a noradrenergic disorder," Biol psychatry. 46(9): 1234-1242 (1999).
Calipari et al., "Amphetamine mechanisms and actions at the dopamine terminal revisited," J Neurosci. 33: 8923-8295 (2013).
Mulder et al., "Cyclic somatostatin analogues as potent antagonists at mu-, but not delta- and kappa-opioid receptors mediating presynaptic inhibition of neutrotransmitter release in the brain," Eur J Pharmacol. 205(1): 1-6 (1991) (1 page) (Abstract Only).
Spencer et al., "The mixed opioid receptor antagonist naltrexone mitigates stimulant-induced euphoria: a double-blind, placebo-controlled trial of naltrexone," J Clin Psychiatry. 79(2): e1-e9 (2018) (9 pages).
Volkow et al., "Mechanism of action of methylphenidate: Insights from PET imaging studies," J Atten Disord. 6(Supplement 1): S31-S43 (2002).
Arnold LE, "Methylphenidate vs. amphetamine: Comparative review," Journal of Attention Disorders. 3(4):200-211 (2000).
Challman et al., "Methylphenidate: its pharmacology and uses," Mayo Clin Proc. 75(7):711-21 (2000).

\* cited by examiner

METHODS AND COMPOSITIONS TO PREVENT ADDICTION

CROSS-REFERENCE TO RELATED APPLICATIONS

This application is a continuation application of co-pending U.S. patent application Ser. No. 13/389,959 filed on Apr. 27, 2012, which is a 35 U.S.C. § 371 National Phase Entry Application of International Application No. PCT/US2010/045486 filed on Aug. 13, 2010, which designated the United States, and which claims the benefit under 35 U.S.C. § 119(e) of U.S. Provisional Application No. 61/233,686, filed Aug. 13, 2009, the contents of each of which are incorporated herein by reference in their entireties.

GOVERNMENTAL SUPPORT

This invention was made with Government support under research grant RO1DA020796 awarded by the National Institutes of Health. The Government has certain rights in the invention.

FIELD OF THE INVENTION

The present invention relates to the field of drug therapies and the prevention of addiction to drugs such as those that activate the dopamine receptor.

BACKGROUND OF THE INVENTION

Methylphenidate (MPH) is the most commonly prescribed stimulant compound for treatment of attention deficit hyperactivity disorder (ADHD)[1,2]. Although its therapeutic efficacy and safety is well documented in pediatric and adult patients[3], serious concerns persist about its abuse potential upon long-term usage[4-9]. Moreover, recreational or street-use of stimulants and analeptics is on the rise further adding to the concerns about stimulant abuse[8,10,11]. In fact, non-human primates can self-administer MPH[12,13]—a hallmark of addiction. Prevailing notions of molecular mechanisms mediating MPH addiction rely on the central actions of MPH on dopamine and noradrenaline signaling mechanisms[14-17]. However, these neurotransmitter mechanisms alone are inadequate for fully explaining MPH addiction.

SUMMARY OF THE INVENTION

One aspect of the invention is a pharmaceutical composition comprising a central nervous system (CNS) stimulant and an opioid receptor antagonist. In one embodiment of the pharmaceutical compositions described herein, the opioid receptor antagonist is selected from the group consisting of naltrexone, naloxone, diprenorphine, etorphine, dihydroetorphine, and combinations thereof. In one embodiment of the various pharmaceutical compositions described herein, the CNS stimulant is selected from the group consisting of methylphenidate, amphetamine, modafinil, and combinations thereof. In one embodiment of the various pharmaceutical compositions described herein, the CNS stimulant is present in a therapeutic amount and the opioid receptor antagonist is present in an amount for preferred inhibition of the mu opioid receptor. In one embodiment of the various pharmaceutical compositions described herein, the composition is formulated for enteral administration. In one embodiment of the various pharmaceutical compositions described herein, the pharmaceutical composition is formulated for oral administration. In one embodiment of the various pharmaceutical compositions described herein, the pharmaceutical composition is formulated as a tablet or capsule. In one embodiment of the various pharmaceutical compositions described herein, the opioid receptor antagonist is formulated such that when ingested, the opioid receptor antagonist remains intact. The various pharmaceutical compositions described herein are suitable for use in the methods described herein.

Another aspect of the invention relates to a method of reducing or preventing the development of aversion to a CNS stimulant in a subject comprising, administering a therapeutic amount of the neurological stimulant and administering an antagonist of the kappa opioid receptor, to thereby prevent the development of aversion to the CNS stimulant in the subject. In one embodiment of the methods described herein, the method further comprises selecting a subject at risk for the development of aversion to the CNS stimulant, prior to the administering. In one embodiment of the methods described herein, the subject is diagnosed with attention deficit hyperactivity disorder (ADHD), narcolepsy, chronic fatigue syndrome, or depression.

Another aspect of the invention relates to a method to decrease the dysphoria associated with the use of therapeutic doses of a CNS stimulant comprising administering a therapeutic amount of the CNS stimulant and administering a kappa opioid receptor antagonist, to thereby decrease the dysphoria. In one embodiment of the methods described herein, the method further comprises selecting a subject at risk for the development of dysphoria, prior to administering.

Another aspect of the invention relates to a method to decrease the euphoria associated with the use of therapeutic doses of a CNS stimulant comprising administering a therapeutic amount of the CNS stimulant and administering a mu opioid receptor antagonist, to thereby decrease the euphoria. In one embodiment of the methods described herein, the method further comprises selecting a subject at risk for the development of euphoria, prior to administering.

Another aspect of the invention relates to a method of reducing or preventing the development of addiction to a CNS stimulant in a subject, comprising, administering the CNS stimulant and administering a mu opioid receptor antagonist to thereby reduce or prevent the development of addiction to the CNS stimulant in the subject. In one embodiment of the methods described herein, the method further comprises selecting a subject at risk for the development of addiction to the CNS stimulant, prior to the administering.

Another aspect of the invention relates to a method of treating a subject for ADHD, comprising administering a therapeutically effective amount of methylphenidate and administering an opioid receptor antagonist to thereby treat the subject for ADHD. In one embodiment of the methods described herein, the method further comprises selecting a subject at risk for the development of aversion or addiction to methylphenidate, prior to the administering.

In one embodiment of the various methods described above, the CNS stimulant is selected from the group consisting of methylphenidate, amphetamine, modafinil, and combinations thereof. In one embodiment of the various methods described above, the CNS stimulant results in activation of a dopamine receptor. In one embodiment, the dopamine receptor is selected from the group consisting of D1, D2, D3, D4, D5, and combinations thereof.

In one embodiment of the various methods described above, the opioid receptor antagonist is selected from the group consisting of naltrexone, naloxone, diprenorphine, etorphine, dihydroetorphine, and combinations thereof. In one embodiment of the various methods described above, the administering is oral. In one embodiment of the various methods described above, the CNS stimulant and the opioid receptor antagonist are administered in the same pharmaceutical composition. In one embodiment of the various methods described above, the CNS stimulant and the opioid receptor antagonist are administered sequentially. In one embodiment of the various methods described above, the opioid receptor antagonist is administered in the dosage of from about 50 to about 100 mg.

Definitions

As the term is used herein, reduce or reducing, as used in connection with reducing dysphoria or reducing euphoria, refers to a reduction or decrease in the dysphoric or euphoric effects experienced by the subject with administration of the drug. A reduction is determined as a statistically significant, detectable, reproducible, decrease, as measured by one or more accepted methods of detection. Dysphoric effects can include, without limitation, an abnormal mood state of feeling unwell, unhappy, uncomfortable, irritable, disliking and anxious. Euphoria effects can include, without limitation, an abnormal mood state of feeling elation, abnormal happiness, severe excitement, abnormal joy not connected to objective circumstances.

Reduce or reducing, as used with respect to reducing drug aversion, or reducing drug addiction, refers to a decrease or lessening of the aversion or addiction. Such a decrease can be evidenced, for example, by preventing or delaying the onset of the development of symptoms of drug aversion or addiction.

As the term is used herein, aversion, refers to avoidance of or failure to adhere to a prescribed regimen of a therapeutic composition, due to the negative effects (dysphoria) experienced therefrom.

As used herein, the term effective amount, refers to an amount of a drug or agent that produced the desired result (e.g, partial or complete inhibition of one or more opioid receptors (mu or kappa). In one embodiment, an effective amount is an amount that preferentially inhibits one opioid receptor without substantially inhibiting another opioid receptor. For example, preferentially inhibiting the MOPR without substantially inhibiting the KOPR, or vice versa.

As used herein the terms subject and patient are used interchangeably, and refer to a recipient in need of the therapy described herein. In one embodiment, the subject is a human. In one embodiment the human is mature (e.g., at least 18 years of age). In one embodiment, the human is immature (e.g., less than 18 years of age), also referred to herein as a child. Subject further refers to mammals such as rats, mice, rabbits, sheep, cats, dogs, cows, pigs, horses and non-human primates.

BRIEF DESCRIPTION OF THE DRAWINGS

In FIG. 1A, time spent in the drug-paired chamber during the pre-conditioning (PC) and test (Test) sessions was calculated and the difference between the two was compared for each drug treatment group. Mice exposed to cocaine or high-dose MPH and cocaine spent significantly longer period of time in the drug-paired chamber during the test sessions compared to the PC sessions (t-test; $p<0.05$). There was no statistically significant difference in this measure for the saline and low dose MPH groups (t-test; $p>0.05$). In FIG. 1B, one-way ANOVA showed significant ($F=6.7$; $p<0.01$) effects of drug treatment on the CPP score (FIG. 1B). Multiple comparisons test showed that the CPP scores were significantly higher ($p<0.05$) in the cocaine and high dose MPH groups compared to the saline and low dose MPH groups (FIG. 1B). There was no significant difference between the cocaine and high dose MPH groups.

In FIG. 2A, [$^{35}$S]GTPγS binding using increasing concentrations of the MOPR agonist DAMGO was examined in the presence of 200 mM GDP, 5 mM $Mg^{++}$ and 100 mM $Na^+$ (A). [$^{35}$S]GTPγS binding was increased by DAMGO in a concentration-dependent manner with an $EC^{50}$ of ~1 and 0.1 μM. The maximal binding, which represented 1.75-fold of the basal level was reached at 10 μM concentration (FIG. 2A). This concentration of DAMGO was used in the bindings assays from the 4 groups of mice shown in FIG. 2B. ANOVA revealed significant effects of the drug treatment (Caudate putamen: $F=5.89$; $p<0.05$; nucleus accumbens: $F=3.3$, $p<0.05$) on DAMGO stimulated [$^{35}$S]GTPγS binding and multiple comparisons analysis showed that the cocaine and high dose MPH groups showed significantly higher MOPR activity compared to the saline or low dose MPH groups ($p<0.05$) in both the brain regions. There was no significant difference between the cocaine and high dose MPH groups.

In FIG. 3A, when the difference in time spent in the drug-paired chamber during the pre-conditioning (PC) and test (Test) sessions was analyzed, high dose of MPH alone produced significant increase (t-test; $p<0.05$) in this measure. Neither saline alone nor naltrexone (1 or 10 mg/kg) alone produced significant changes in this measurement (i.e. did not induce CPP). When naltrexone (1, 5 or 10 mg/kg) was administered prior to MPH, in each case there was a significant difference between PC and Test sessions ($p<0.05$) indicating that each drug treatment had induced CPP. In FIG. 3B, when the CPP scores were compared among the experimental groups, a significant effect of drug treatment was found (ANOVA; $F=9.78$, $p<0.001$). Comparisons between the different groups showed that prior treatment with 1, 5 or 10 mg/kg naltrexone significantly decreased the CPP score compared to the CPP score produced when MPH was administered alone. The decrease in the CPP score was naltrexone dose-dependent. In fact, the CPP score for the group that had received the highest dose of naltrexone (10 mg/kg) prior to MPH was not significantly different from that for the saline group. In FIG. 3C, agonist-stimulated MOPR activity was analyzed using the [$^{35}$S]GTPγS binding in membrane preparations of the caudate-putamen and nucleus accumbens from the saline alone, MPH (7.5 mg/kg) alone and MPH+naltrexone (10 mg/kg) groups of mice that had been used in the CPP assay. ANOVA revealed significant effects of the drug treatment (caudate putamen; F=66.17; p<0.0001; nucleus accumbens; F=45.88, p<0.0001) and multiple comparisons analysis showed that the MOPR activity in the MPH+naltrexone (10 mg/kg) group was significantly lower compared to that in the saline or MPH alone groups (p<0.01).

In FIG. 4A, when the difference in time spent in the drug-paired chamber during the pre-conditioning (PC) and test (Test) sessions was analyzed, high dose MPH alone and MPH+ reclopride and no other drug treatment produced significant increase (t-test; p<0.05) in this measure. In FIG. 4B, when differences in CPP score were compared among the different groups, significant effect of the drug treatment was observed (ANOVA; F=9.3; p<0.0001). Multiple comparisons test showed that the MPH+Schering 23390 group had significantly lower CPP score (p<0.01) compared to the MPH only group and that there was no statistically significant difference between saline and MPH+Schering 23390 groups. The MPH only and MPH+raclorpide groups did not show significant differences.

DETAILED DESCRIPTION OF THE INVENTION

Figure 1A:
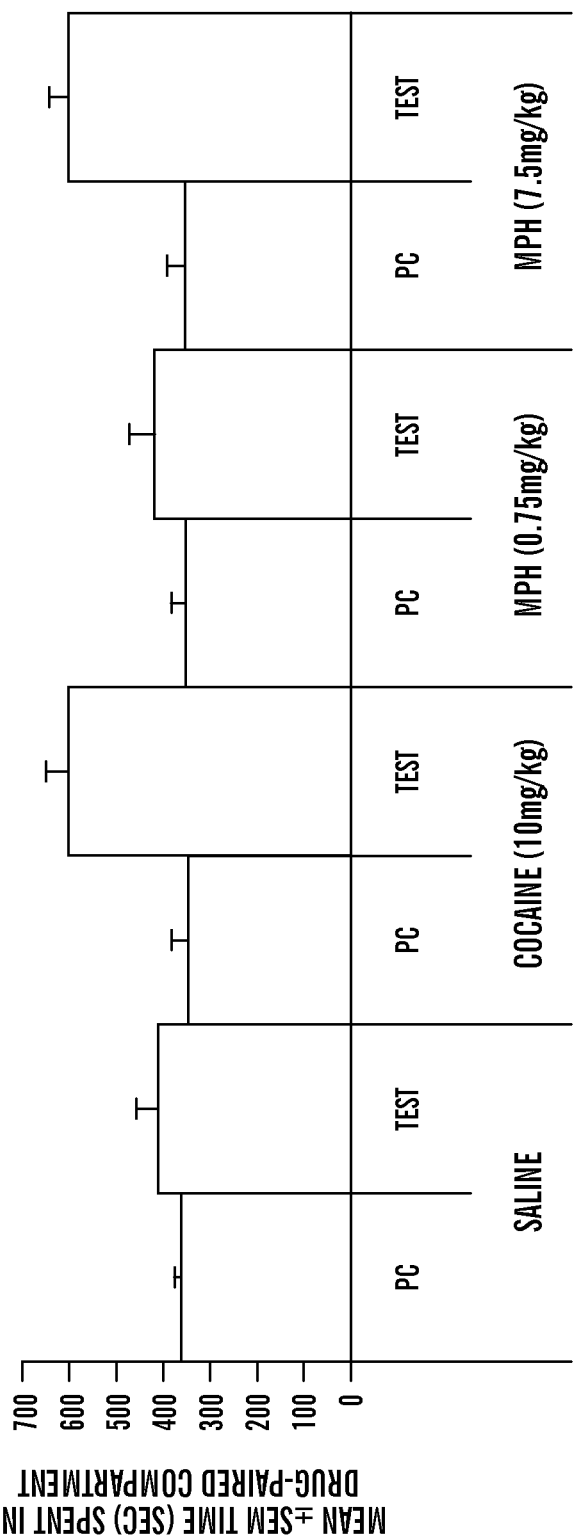
FIG. 1A-1B are graphical representations of experimental results that indicate supratherapeutic doses of methylphenidate (MPH) induce conditioned place preference (CPP). CPP induced by intraperitoneal administration of saline (negative control), low dose (0.75 mg/kg) MPH, high dose (7.5 mg/kg) MPH and cocaine (10 mg/kg; positive control) was analyzed.

Aspects of the present invention relate to methods for reducing or preventing dysphoria in a subject associated with administration of a therapeutic amount of a drug to the subject, by administering an effective amount of an agent that inhibits the kappa opioid receptor to the subject, to thereby reduce or prevent dysphoria in the subject. The reduction of dysphoria is expected to reduce the development of aversion to the drug by the subject, and to therefore promote adhereance by the subject to a prescribed therapeutic regimen. As such, another aspect of the invention relates to a method of reducing or preventing the development of aversion to a drug in a subject. The method comprises administering a therapeutic amount of the drug and administering an effective amount of an agent that inhibits the kappa opioid receptor, to thereby reduce or prevent the development of aversion to the drug in the subject.

In one embodiment, a subject is first identified or selected as a subject at risk for the development of dysphoria or aversion to the drug, prior to the administration of the drug and the agent.

Aspects of the present invention relate to methods for reducing or preventing euphoria in a subject associated with administration of a therapeutic amount of a drug to the subject, by administering an effective amount of an agent that inhibits the mu opioid receptor to the subject, to thereby reduce or prevent euphoria in the subject. The reduction of euphoria is expected to reduce the development of addiction to the drug by the subject. As such, another aspect of the invention relates to a method of reducing or preventing the development of addiction to a drug in a subject. The method comprises administering a therapeutic or supratherapeutic amount of the drug and administering an effective amount of an agent that inhibits the mu opioid receptor, to thereby reduce or prevent the development of addiction to the drug in the subject.

In one embodiment of the method, the subject is first identified or selected as a subject at risk for the development of euphoria or addiction to the drug, prior to the administration of the drug and the agent.

Another aspect of the present invention is a method of treating a subject for a disease or disorder typically treated with a drug discussed herein. The method involves administering the drug to the subject and administering an agent that inhibits an opioid receptor (mu and/or kappa), to the subject, to thereby treat the subject for the disease or disorder. The agent is administered in an amount effective to inhibit the mu and/or kappa opioid receptor. In one embodiment, the subject is diagnosed with the disease or disorder prior to treatment. In another embodiment, the subject is identified as at risk for the development of euphoria/addiction or dysphoria/aversion, prior to the administering of a mu or kappa opioid receptor inhibitor, respectively. In one embodiment, the disease or disorder is attention deficit hyperactivity disorder, narcolepsy, chronic fatigue syndrome, or depression, and the drug is methylphenidate. In one embodiment, the agent is naltrexone, naloxone, diprenorphine, etorphine, dihydroetorphine or combinations thereof. In one embodiment the disease or disorder is age-related memory decline, attention deficit disorder, depression, fatigue caused by high-pressure jobs requiring long hours, fatigue caused by chemotherapy treatment for cancer patients, fatigue experienced by persons suffering from diseases such as multiple sclerosis, fatigue experienced by people who need to be awake and alert for extended amounts of times such as soldiers, truckers or students cramming for finals, jet lag, memory problems associated with Alzheimer's disease, post-anesthesia grogginess, sleepiness caused by other prescription medications, or treatment for cocaine addiction, and the drug is modafinil.

Subjects who are at risk for the development of aversion or addiction can be identified by a variety of means known in the art. Subjective drug experience, especially euphoria, is thought to be an indicator of risk of abuse (Jasinski and Henningfield, 1989; Jasinski, 2000; Kollins et al., 2001) and dysphoria is thought to be a major determinant of tolerability and adherence with treatment regimen in clinical practice. Subjective responses to oral MPH were reported in 18 (72%) of 25 studies that evaluated detection/likeability (Kollins et al., 2001). Likewise the large extent of clinical trials literature documents the frequent occurrence of dysphoric effects in clinical populations that adversely impact tolerability and eventually compliance with stimulant treatment.

Subjects who are at risk for the development of aversion or addiction can be identified, for example, by assessment of the subjects dysphoric or euphoric response, respectively, to the drug by established methods. Assessment of euphoria and dysphoria can be assessed in a subject, for example, by assessing the subjective response of euphoria (liking) and dysphoria (disliking) of acute oral therapeutic doses of the drug using the Drug Rating Questionnaire (DQRS), (Jasinski and Henningfield, 1989; Jasinski, 2000; Kollins et al., 2001). Constituent elements of the DQRS scale have been standardized by comparison to responses to known drugs of abuse and validated against observer ratings and physiologic changes (Jasinski and Henningfield, 1989). Subjects who experience dysphoria or euphoria in connection with a specific drug, are likely to have the same or even an enhanced experience, upon repeated exposure to the drug. As such, the assessment is also useful in identifying a subject at risk for ongoing dysphoria or euphoria associated with the drug. In some circumstances, assessment of euphoria and dysphoria to a drug similar (e.g., in mode of action) to the intended therapeutic prescribed drug will also yield useful information regarding a subject's likelihood of developing dysphoria and/or aversion, or euphoria and/or addiction. Another method of identifying a subject at risk for aversion/dysphoria or addiction/euphoria is by analysis of the subject's history with other drugs. In one embodiment, a subject with a history or drug aversion/dysphoria, or drug addiction/euphoria, to other drugs, is identified as at risk.

Drugs for which the herein described methods are appropriate include, without limitation, CNS stimulants, drugs which activate one or more dopamine receptors, and analeptics. In one embodiment, the drug is methylphenidate, amphetamine, or modafinil.

Agents that inhibit the respective opioid receptors described herein include, without limitation, agents that work directly (e.g., antagonists of the receptors) and also agents that work indirectly (e.g., agents that inhibit signaling from the receptor or agents that inhibit expression of the receptors). Examples of such agents are described herein. In one embodiment, the agent is naltrexone, naloxone, diprenorphine, etorphine, dihydroetorphine or combinations thereof.

Another aspect of the present invention relates to pharmaceutical compositions comprising both the drug and the agent for inhibition of opioid receptor, described in the methods herein. A pharmaceutical composition includes one or more active agents, formulated appropriately for the desired route of administration, and a pharmaceutically acceptable carrier(s) and/or excipient(s) suitable for the desired route of administration. As used herein, "pharmaceutically acceptable carrier" includes any and all solvents, dispersion media, coatings, antibacterial and anti fungal agents, isotonic and absorption delaying agents, and the like that are physiologically compatible. For example, the carrier can be suitable for intravenous injection or for oral administration. Excipients include pharmaceutically acceptable stabilizers and disintegants. In one embodiment, the pharmaceutical composition of the present invention is formulated for enteral or oral administration. In one embodiment, the pharmaceutical composition is formulated as a tablet or capsule.

In one embodiment, the drug is a CNS stimulant, a drug which actives one or more dopamine receptors, an analeptic, or combinations thereof. In one embodiment, the drug is methylphenidate, amphetamine, or modafinil.

In one embodiment, the agent for inhibition of opioid receptor is naltrexone, naloxone, diprenorphine, etorphine, dihydroetorphine, or combinations thereof.

In one embodiment, the drug (e.g., CNS stimulant) is present in a therapeutic amount and the opioid receptor antagonist is present in an amount for preferred inhibition of a specific opioid receptor (e.g., MOPR). For example, a low dose, as described herein can be included in the pharmaceutical composition with the drug (e.g, methylphenidate). The exact amount of the opioid receptor inhibitor can be determined from the amount of the drug in the composition, since the amount of the drug will determine the amount and frequency of therapeutic administration of the pharmaceutical composition.

A drug formulated in combination with the mu opioid receptor inhibitor has the advantage that it will be "less-abusable" or "non-abusable". That is to say, the euphoric effects experience are substantially reduced or eliminated. As such, the formulations described herein would be less attractive for illegal, non-therapeutic administration, and also far less likely to cause addition in a subject who was self-administering for non-therapeutic purposes. Such effective formulations could theoretically avoid the requirement for classification as a Schedule II drug. This would make them more readily available and more easily obtained for therapeutic purposes.

In one embodiment, the pharmaceutical composition comprises the drug (e.g., methylphenidate) and the opioid receptor inhibitor (e.g., naltrexone), formulated to prevent MPH abuse potential without affecting the development of dysphoria/aversion in a subject. A recent technology is used in which an oral preparation (capsule or tablet) is prepared with naltrexone embedded in the core surrounded by MPH. When the capsules/tablets are ingested only MPH is released and the naltrexone core passes through the gut intact. This technology is available commercially (AVERSION©, Acura Pharmaceuticals; Embeda®, King Pharmaceuticals). In such preparations, MPH exerts its actions without naltrexone interference. However, if the preparation is crushed for intra-nasal administration or other abuse purposes, naltrexone is released blocking MPH addiction. This approach will not help prevent MPH aversion, but can prevent abuse and addiction.

Central Nervous System (CNS) Stimulants

CNS stimulants (also called psychostimulants) are psychoactive drugs which induce temporary improvements in either mental or physical function or both. In one embodiment, CNS stimulants include, but not limited to, caffeine, nicotine, cocaine, amphetamine, dextroamphetamine. L-amphetamine, methamphetamine, methylenedioxymethamphetamine (MDMA), norepinephrine reuptake inhibitors (NRIs) norepinephrine-dopamine reuptake inhibitors (NDRIs), Modafinil, ampakines, yohimbine, phencyclidine, phenmetratzine, methylphenidate, diethylpropion, pemoline, mazindol, (−) cathione, fenfluramine (and other amphetamine derivatives having substitutions in aromatic ring). Further exemplary CNS stimulants are shown in Table 1:

TABLE 1

| | Examples of types of CNS stimulants |
|---|---|
| Adamantanes | Adaphenoxate • Adapromine • Amantadine • Bromantane • Chlodantane • Gludantane • Memantine • Midantane |
| Arylcyclohexylamines | Benocyclidine • Dieticyclidine • Esketamine • Eticyclidine • Gacyclidine • Ketamine • Phencyclamine • Phencyclidine • Rolicyclidine • Tenocyclidine • Tiletamine |
| Benzazepines | 6-Br-APB • SKF-77434 • SKF-81297 • SKF-82958 |
| Cholinergics | A-84543 • A-366,833 • ABT-202 • ABT-418 • AR-R17779 • Altinicline • Anabasine • Arecoline • Cotinine • Cytisine • Dianicline • Epibatidine • Epiboxidine • GTS-21 • Ispronicline • Nicotine • PHA-543,613 • PNU-120,596 • PNU-282,987 • Pozanicline • Rivanicline • Sazetidine A • SIB-1553A • SSR-180,711 • TC-1698 • TC-1827 • TC-2216 • TC-5619 • Tebanicline • UB-165 • Varenicline • WAY-317,538 |
| Convulsants | Anatoxin-a • Bicuculline • DMCM • Flurothyl • Gabazine • Pentetrazol • Picrotoxin • Strychnine • Thujone |
| Eugeroics | Adrafinil • Armodafinil • CRL-40941 • Modafinil |
| Oxazolines | 4-Methylaminorex • Aminorex • Clominorex • Cyclazodone • Fenozolone • Fluminorex • Pemoline • Thozalinone |
| Phenethylamines | 1-(4-Methylphenyl)-2-aminobutane • 2-Fluoroamphetamine • 2-Fluoromethamphetamine • 2-OH-PEA • 2-Phenyl-3-aminobutane • 2-Phenyl-3-methylaminobutane • 2,3-MDA • 3-Fluoroamphetamine • 3-Fluoroethamphetamine • 3-Fluoromethcathinone • 3-Methoxyamphetamine • 3-Methylamphetamine • 4-BMC • 4-Ethylamphetamine • 4-FA • 4-FMA • 4-MA • 4-MMA • 4-MTA • 6-FNE • Alfetamine • α-Ethylphenethylamine • Amfecloral • Amfepentorex • Amfepramone • Amidephrine • Amphetamine (Dextroamphetamine, Levoamphetamine) • Amphetaminil • Arbutamine • Atomoxetine (Tomoxetine) • β-Methylphenethylamine • β-Phenylmethamphetamine • Benfluorex • Benzphetamine • BDB (J) • BOH (Hydroxy-J) • BPAP • Buphedrone • Bupropion (Amfebutamone) • Butylone • Cathine • Cathinone • Chlorphentermine • Clenbuterol • Clobenzorex • Cloforex • Clortermine • D-Deprenyl • Denopamine • Dimethoxyamphetamine • Dimethylamphetamine • Dimethylcathinone (Dimethylpropion, Metamfepramone) • Dobutamine • DOPA (Dextrodopa, Levodopa) • Dopamine • Dopexamine • Droxidopa • EBDB (Ethyl-J) • Ephedrine • Epinephrine (Adrenaline) • Epinine (Deoxyepinephrine) • Etafedrine • Ethcathinone (Ethylpropion) • Ethylamphetamine (Etilamfetamine) • Ethylnorepinephrine (Butanefrine) • Ethylone • Etilefrine • Famprofazone • Fenbutrazate • Fencamine • Fencamfamine • Fenethylline • Fenfluramine (Dexfenfluramine) • Fenproporex • Flephedrone • Fludorex • Furfenorex • Gepefrine • HMMA • Hordenine • Ibopamine • IMP • Indanylamphetamine • Isoetarine • Isoprenaline (Isoproterenol) • L-Deprenyl (Selegiline) • Lefetamine • Lisdexamfetamine • Lophophine (Homomyristicylamine) • Manifaxine • MBDB (Methyl-J; "Eden") • MDA (Tenamfetamine) • MDBU • MDEA ("Eve") • MDMA ("Ecstasy", "Adam") • MDMPEA (Homarylamine) • MDOH • MDPR • MDPEA (Homopiperonylamine) • Mefenorex • Mephedrone • Mephentermine • Metanephrine • Metaraminol • Methamphetamine (Desoxyephedrine, Methedrine; Dextromethamphetamine, Levomethamphetamine) • Methoxamine • Methoxyphenamine • MMA • Methcathinone (Methylpropion) • Methedrone • Methoxyphenamine • Methylone • MMDA • MMDMA • MMMA • Morazone • Naphthylamphetamine • Nisoxetine • Norepinephrine (Noradrenaline) • Norfenefrine • Norfenfluramine • Normetanephrine • Octopamine • Orciprenaline • Ortetamine • Oxilofrine • Paredrine (Norpholedrine, Oxamphetamine, Mycadrine) • PBA • PCA • PHA • Pargyline • Pentorex (Phenpentermine) • Pentylone • Phendimetrazine • Phenmetrazine • Phenpromethamine • Phentermine • Phenylalanine • Phenylephrine (Neosynephrine) • Phenylpropanolamine • Pholedrine • PIA • PMA • PMEA • PMMA • PPAP • Prenylamine • Propylamphetamine • Pseudoephedrine • Radafaxine • Ropinirole • Salbutamol (Albuterol; Levosalbutamol) • Sibutramine • Synephrine (Oxedrine) • Theodrenaline • Tiflorex (Flutiorex) • Tranylcypromine • Tyramine • Tyrosine • Xamoterol • Xylopropamine • Zylofuramine |
| Piperazines | 2C-B-BZP • BZP • CM156 • DBL-583 • GBR-12783 • GBR-12935 • GBR-13069 • GBR-13098 • GBR-13119 • MeOPP • MBZP • Vanoxerine |
| Piperidines | 1-Benzyl-4-(2-(diphenylmethoxy)ethyl)piperidine • 2-Benzylpiperidine • 3,4-Dichloromethylphenidate • 4-Benzylpiperidine • 4-Methylmethylphenidate • Desoxypipradrol • Difemetorex • Diphenylpyraline • Ethylphenidate • Methylnaphthidate • Methylphenidate (Dexmethylphenidate) • Nocaine • Phacetoperane • Pipradrol • SCH-5472 |
| Pyrrolidines | α-PPP • α-PBP • α-PVP • MDPPP • MDPBP • MDPV • MPBP • MPHP • MPPP • MOPPP • Naphyrone • PEP • Prolintane • Pyrovalerone |

TABLE 1-continued

Examples of types of CNS stimulants

| | |
|---|---|
| Tropanes | 3-CPMT • 3-Pseudotropyl-4-fluorobenzoate • 4'-Fluorococaine • AHN-1055 • Altropane (IACFT) • Brasofensine • CFT (WIN 35,428) • β-CIT (RTI-55) • Cocaethylene • Cocaine • Dichloropane (RTI-111) • Difluoropine • FE-β-CPPIT • FP-β-CPPIT • Ioflupane ($^{123}$I) • Norcocaine • PIT • PTT • RTI-31 • RTI-32 • RTI-51 • RTI-105 • RTI-112 • RTI-113 • RTI-117 • RTI-121 (IPCIT) • RTI-126 • RTI-150 • RTI-154 • RTI-171 • RTI-177 • RTI-183 • RTI-194 • RTI-202 • RTI-229 • RTI-241 • RTI-336 • RTI-354 • RTI-371 • RTI-386 • Salicylmethylecgonine • Tesofensine • Troparil (β-CPT, WIN 35,065-2) • Tropoxane • WF-23 • WF-33 • WF-60 |
| Xanthines | Aminophylline • Caffeine • Dimethazan • Paraxanthine • Theobromine • Theophylline |
| Others | 1-(Thiophen-2-yl)-2-aminopropane • 2-Amino-1,2-dihydronaphthalene • 2-Aminoindane • 2-Aminotetralin • 2-Diphenylmethylpyrrolidine • 2-MDP • 3,3-Diphenylcyclobutanamine • 5-(2-Aminopropyl)indole • 5-Iodo-2-aminoindane • AL-1095 • Amfonelic acid • Amineptine • Amiphenazole • Atipamezole • Bemegride • Benzydamine • BTQ • BTS 74,398 • Carphedon • Ciclazindol • Cilobamine • Clofenciclan • Cropropamide • Crotetamide • Diclofensine • Dimethocaine • Diphenylprolinol • Efaroxan • Etamivan • EXP-561 • Fenpentadiol • Feprosidnine • Gamfexine • Gilutensin • GYKI-52895 • Hexacyclonate • Idazoxan • Indanorex • Indatraline • JNJ-7925476 • JZ-IV-10 • Lazabemide • Leptacline • Levopropylhexedrine • LR-5182 • Mazindol • Meclofenoxate • Medifoxamine • Mefexamide • Mesocarb • Nefopam • Nikethamide • Nomifensine • O-2172 • Oxaprotiline • Phthalimidopropiophenone • PNU-99,194 • Propylhexedrine • PRC200-SS • Rasagiline • Rauwolscine • Rubidium chloride • Setazindol • Tametraline • Tandamine • Trazium • UH-232 • Yohimbine |

In one embodiment, the CNS stimulants is an antidepressant. Antidepressant drugs include the monoamine oxidase inhibitors (MAOIs), tricyclic antidepressants (TCAs), tetracyclic antidepressants (TeCAs), selective serotonin reuptake inhibitors (SSRIs), and serotonin-norepinephrine reuptake inhibitors (SNRIs). In another embodiment, CNS stimulants include psychostimulants, agents for treatment of ADHD, or nootropics (cognitive enhancers). Examples of these types of CNS stimulants are shown in Table 2.

TABLE 2

Examples of psychostimulants, drugs for treatment of ADHD and nootropics

| | | |
|---|---|---|
| Centrally acting sympathomimetics | Amphetamine • Amphetaminil • Atomoxetine • Dextroamphetamine • Dextromethamphetamine • Fencamfamine • Fenethylline • Lisdexamfetamine • Methylphenidate • Mesocarb • Pemoline • Pipradrol • Prolintane | |
| Xanthine derivatives | Caffeine • Fenethylline | |
| Glutamate receptor | Racetams | Aniracetam • Nefiracetam • Noopept • Oxiracetam • Phenylpiracetam • Piracetam • Pramiracetam |
| | Ampakines | CX-516 • CX-546 • CX-614 • CX-691 • CX-717 • IDRA-21 • LY-404,187 • LY-503,430 • PEPA • S-18986 • Sunifiram • Unifiram |
| Eugeroics/ Benzhydryl compounds | Adrafinil • Armodafinil • Modafinil | |
| Histamine H3 receptor antagonists | A-349,821 • ABT-239 • Ciproxifan • GSK-189,254 | |
| GABA$_A$ α$_5$ inverse agonists | α5IA • L-655,708 • PWZ-029 • Suritozole • TB-21007 • ZK-93426 | |
| Dopamine D1 receptor agonists | A-77636 • Dihydrexidine • Dinapsoline • Doxanthrine • SKF-81297 • 6-Br-APB | |
| α7 nicotinic agonists/ PAMs | AR-R17779 • PNU-282,987 • SSR-180,711 | |
| Prolyl endopeptidase inhibitors | S-17092 | |
| Other psychostimulants and nootropics | Acetylcarnitine • Adafenoxate • Bifemelane • Carbenoxolone • Citicoline • Cyprodenate • Ensaculin • Idebenone • Ispronicline • Deanol • Dimebon • Fipexide • Leteprinim • Linopirdine • Meclofenoxate • Nizofenone • P7C3 • Pirisudanol • Pyritinol • Rubidium • Sulbutiamine • Taltirelin • Tricyanoaminopropene • Vinpocetine | |

Analeptics

The methods and compositions described herein, as they relate to CNS stimulants, can also be used to reduce the dysphoria and euphoria associated with administration of analeptics. As such, another aspect of the invention relates to the use of opioid receptor antagonists to reduce the dysphoria and euphoria associated with analeptic therapeutic and supratherapeutic administration.

Analeptics are drugs that principally act as or are used as a central nervous system stimulant. Some examples are, but not limited to, modafinil and d-amphetamine. In one embodiment, the analeptic activates one or more dopamine receptors. Analeptics may also be respiratory analeptics (e.g., respiratory stimulants) such as picrotoxin, pentylenetetrazol, caffeine, theophylline, strychnine, ethamivan and doxapram. which activates other receptors, (e.g., chemoreceptors, GABAA receptor or glycine receptors in central nervous system).

Administration and Formulations

The compositions described herein are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

The pharmaceutical compositions of the present invention may be administered in a number of ways depending upon whether local or systemic treatment is desired. Administration may be topical (including ophthalmic, vaginal, rectal, intranasal, epidermal, and transdermal), enteral (e.g., oral) or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compositions of the invention are formulated into conventional oral administration forms such as capsules, tablets and tonics.

Administration of the drug (e.g., methylphenidate) and the agent that inhibits opioid receptor (e.g., opioid receptor antagonist) can be at the same time (co-administration), or at different times (e.g., sequentially). Co-administration can be in the same therapeutic formulation, or in different formulations, by the same or different routes. In one embodiment, the drug is administered at different times, and at different rates of frequency than the opioid receptor inhibiting agent.

Suitable formulations for the compositions described herein are those appropriate for the desired route of administration.

Orally administered compositions may take the form of, for example, liquids, beverages, tablets, capsules, lozenges, aqueous or oily suspensions, dispersible powders or granules, emulsions, syrups, or elixirs. Compositions intended for oral use may be prepared according to any method known in the art, and such compositions may contain one or more agents such as sweetening agents, flavoring agents, coloring agents, and preserving agents. They may also contain one or more additional ingredients such as vitamins and minerals, etc. Tablets may be manufactured to contain one or more active ingredients described herein, in admixture with non-toxic, pharmaceutically acceptable excipients that are suitable for the manufacture of tablets. These excipients may be, for example, inert diluents, granulating and disintegrating agents, binding agents, and lubricating agents. The tablets may be uncoated or they may be coated by known techniques to delay disintegration and absorption in the gastrointestinal tract and thereby provide sustained action over a longer period. For example, a time delay material such as glyceryl monostearate or glyceryl distearate may be used.

Methylphenidate is available commercially in a variety of forms. Each version of methylphenidate is envisioned for use in the present invention. Methylphenidate comes as an immediate-release tablet, a chewable tablet, a solution (liquid), an intermediate-acting (extended-release) tablet, a long-acting (extended-release) capsule, and a long-acting (extended-release) tablet. The long-acting tablet and capsules supply some medication immediately and release the remaining amount as a steady dose of medication over a long time. All of these forms of methylphenidate are typically administered orally for therapeutic purposes.

Dosage

Therapeutic dosage and dose regimen of the drugs described herein are known in the art, and can be determined by the skilled practitioner for each individual subject.

For methylphenidate, the dose regimen usually varies with commercially-packaged forms of methylphenidate. The regular tablets, chewable tablets (Methylin), and solution (Methylin) are usually taken two to three times a day by adults and twice a day by children, preferably 35 to 40 minutes before meals. Adults who are taking three doses should take the last dose should be taken before 6:00 pm, so that the medication will not cause difficulty in falling asleep or staying asleep. The intermediate-acting extended release tablets (Ritalin SR, Metadate ER, Methylin ER) are usually taken once or twice a day, in the morning and sometimes in the early afternoon 30-45 minutes before a meal. The long-acting extended release capsule (Metadate CD) is usually taken once a day before breakfast; the long-acting extended-release tablet (Concerta) and capsule (Ritalin LA) are usually taken once a day in the morning with or without food.

The appropriate therapeutic dosage of methylphenidate can be determined by the skilled practitioner. A therapeutic dose for ADHD treatment is typically in the range of about 0.05 mg/kg/day to about 2.0 mg/kg/day, for both children and adults. In one embodiment, about 0.075 mg/kg/day to about 0.3 mg/kg/day is administered. The average total dosage is about 20 to 30 mg daily. Some patients may require about 40 to 60 mg daily. In others, about 10 to 15 mg daily is adequate. For children suffering from ADHD, the initial recommended dosage is about 5 mg twice daily before breakfast and lunch, increased by about 5-10 mg per week to about 60 mg per day. Methylphenidate is typically administered in divided dose 2 or 3 times daily, preferably 30 to 45 minutes before meals. For narcolepsy in adults, the recommended dose is about 5-20 mg two to three times a day, 30-45 minutes before meals.

The effective amount of an agent that inhibits a specific opioid receptor can be determined by the skilled practitioner, from the knowledge in the art and the guidance provided by the Examples section herein. The amount may depend upon the specific opioid receptor(s) to be inhibited. In one embodiment, the dosage is from about 50 to about 100 mg. In one embodiment, the opioid inhibitor is naltrexone.

Dosage may be optimized to result in increased/preferred inhibition of one receptor (e.g., MOPR) over one or more other opioid receptor types (e.g, KOPR and/or DOPR). For example, a low dose of an opioid receptor inhibitor that has a higher affinity for MOPR than for KOPR (e.g., naloxone) is given to a patient to produce an increased inhibition of MOPR, with little to no inhibition of KOPR. As another example a low dose of an opioid receptor inhibitor that has a higher affinity for KOPR than for MOPR is given to a patient to produce an increased inhibition of KOPR, with little to no inhibition of MOPR. As used herein, the term "low dose" refers to dosages given to a patient that are less than about 1.5 µg/kg (drug weight drug/patient weight). In one embodiment, the low dose is about 0.1 ng/kg to about 100 µg/kg. In one embodiment the low dose is between about 0.01 ng/kg and about 1.5 µg/kg, (e.g., between about 0.01 ng/kg and about 150 ng/kg). These dosages may administered one time per day, or 2 to 3 times daily. In some embodiments, one or both of the dosages are administered at night. Other dosing schedules are envisioned. For example, the dosages may be administered less frequently in extended release or controlled delivery formulations. In one embodiment, naltrexone or naloxone is administered in a low dose.

Methylphenidate

Methylphenidate (MPH) is a central nervous system (CNS) stimulant and also an analeptic. Methylphenidate increases dopamine level in the brain by blocking dopamine transporters (classified as a dopamine transporter (DAT) inhibitor or dopamine reuptake (DAR) inhibitor) and thereby enhances the activity of dopamine receptors (Volkow, Journal of Neuroscience 2001, 21: RC121:1-5).

Methylphenidate is most commonly prescribed for the treatment of attention-deficit hyperactivity disorder (ADHD). It is also effective as an anti-fatigue drug and as a stimulant in circumstances requiring extraordinary alertness such as those endured by military pilots flying combat missions. Further, it is used to treat narcolepsy (a sleep disorder that causes excessive daytime sleepiness and sudden attacks of sleep) (Fry et al., Neurology 50 (2 Suppl 1): S43-8). Recent reports have shown that methylphenidate can be used to treat children with autism spectrum disorders to improve their social behaviors (Jahromi et al., J Autism Dev Disord 39 (3): 395-404). Moreover, methylphenidate has been investigated as a chemical replacement for the treatment of cocaine dependence (Grabowski et al., J Clin Psychopharmacol 17 (6): 485-8 1997; Karila et al., Int. J. Neuropsychopharmacol. 11 (3): 425-38). In addition, methylphenidate can be used for adjunctive therapy. For example, methylphenidate can be administered to individuals with cancer in order to ameliorate opioid-induced somnolence, to augment the analgesic effects of opioids, to treat depression, and to improve cognitive function (Rozans et al., J. Clin. Oncol. (1): 335-9). In addition, methylphenidate can be used to improve depression in several groups including stroke, cancer, and HIV-positive patients (Leonard et al., Hum Psychopharmacol 19 (3): 151-80).

Dopamine Receptors

In one embodiment, the drug for which the methods and compositions described herein is appropriate, activates one or more dopamine receptors. Dopamine receptors are members of the G protein-linked receptor family with seven hydrophobic domains, an extracellular N terminus and an intracellular C terminus. They are prominent in the central nervous system (CNS), and the primary endogenous ligand for dopamine receptors is the neurotransmitter dopamine.

There are at least five subtypes of dopamine receptors, $D_1$, $D_2$, $D_3$, $D_4$, and $D_5$. The $D_1$ and $D_5$ receptors are members of the $D_1$-like family of dopamine receptors, whereas the $D_2$, $D_3$ and $D_4$ receptors are members of the $D_2$-like family. At a global level, $D_1$ receptors have widespread expression throughout the brain. Furthermore, $D_{1-2}$ receptor subtypes are found at 10-100 times the levels of the $D_{3-5}$ subtypes (Hurley M J et al., Pharmacol Ther 2006. 111 (3): 715).

The $D_1$ receptor of the central nervous system is defined as an adenylate cyclase stimulatory receptor. The location of the prototypic $D_1$ receptor is the bovine parathyroid gland, where dopamine agonists stimulate cAMP synthesis via adenylate cyclase, accompanied by parathyroid hormone release. Dopamine-stimulated adenylate cyclase activity and parathyroid hormone release are sensitive to both GTP and cholera toxin. This suggests that the $D_1$ receptor is associated with a $G_s$ guanine nucleotide binding protein. The $D_2$ receptor, in contrast, inhibits adenylate cyclase activity, and appears to be the primary target of most neuroleptic drugs (Niznik, H. B. and Jarvie, K. R. (1989). Dopamine receptors, in "Receptor Pharmacology and Function", eds. Williams, M., Glennon, R., and Timmermans, P., Marcel Dekker Inc., New York, pp. 717-768). The prototypic $D_2$ receptor has been characterized in the anterior pituitary where it is associated with the inhibition of release of prolactin and alpha-melanocyte stimulating hormones.

Dopamine Receptor Agonists and Indirect Dopamine Receptor Activators

Drugs that activate, directly or indirectly, one or more dopamine receptors are appropriate for the methods and compositions described herein. These include drugs that active the dopamine receptor directly (e.g., agonists) or indirectly.

Dopamine receptor agonists include, without limitation, pramipexole, ropinirole, bromocriptine, pergolide, preclamol, talipexole, cabergoline, lisuride, roxindole, rotigotine, SDZ 208-911, SDZ 208-912, bifeprunox, aripiprazole, PD 158771, PD128483, N-propylnorapomorphine, apomorphine, sumanirole, aplindore, BP897, CJB090, and RGH237.

Indirect activation of the dopamine receptor can be accomplished, for example, by agents that augment dopamine synthesis, by blocking reuptake of extracellular dopamine into dopamine neurone, or by releasing of dopamine from dopamine neurons. Such agents include, L-DOPA; amphetamine formulations, including formulations of specific stereoisomers such as d-amphetamine; methylphenidate formulations, including formulations of specific stereoisomers; buproprion; serotonin dopamine reuptake inhibitors including but not limited to sertraline; serotonin norepinephrine reuptake inhibitors including but not limited to duloxetine, venlaxafin or desvenlafaxin, triple reuptake inhibitors such as JNJ 7925476, tesofensine, and DOV216303; selective norepinephrine reuptake inhibitors such as but not limited to atomoxetine formulations; as well as atypical antipsychotic drugs such as clozapine, ziprasidone, olanzapine, risperidone, and quetiapine, and the like. Non-limiting examples of drugs that increase the extracellular concentration of dopamine by decreasing metabolic degradation of dopamine include inhibitors of monoamine oxidase and catechol-O-methyl transferase. Examples of such inhibitors include, but are not limited to, phenelzine, tranylcypromine, selegiline, rasagiline, and tolcapone.

Other drugs that work through the dopamine receptor include, without limitation, DAT or DAR inhibitors, such as Amineptine (Survector, Maneon, Directim); Benzatropine/ Benztropine (Cogentin); Bupropion (Wellbutrin, Zyban); Dexmethylphenidate (Focalin); Esketamine (Ketanest S); Etybenzatropine/Ethybenztropine (Panolid, Ponalid, Ponalide); Fencamfamine (Glucoenergan, Reactivan); Fencamine (Altimina, Sicoclor); Ketamine (Ketalar, Ketaset, Ketanest, Ketaject); Lefetamine (Santenol); Medifoxamine (Cledial); Mesocarb (Sidnocarb, Sydnocarb); Methylphenidate (Ritalin, Concerta); Nefopam (Acupan); Nomifensine (Merital); Pipradrol (Meretran); Prolintane (Promotil, Katovit); Pyrovalerone (Centroton, Thymergix); Tiletamine (Telazol, Rompun); Tripelennamine (Pyribenzamine), Cocaine (found in Erythroxylum coca (Coca)); Desoxypipradrol (2-DPMP); Diphenylprolinol (D2PM); Eticyclidine (PCE); Methylenedioxypyrovalerone (MDPV); Phencyclidine (PCP); Rolicyclidine (PCPy); Tenocyclidine (TCP), Altropane (IACFT; O-587); Amfonelic Acid (AFA; WIN-25,978); Benocyclidine (BTCP; GK-13); Brasofensine (NS-2214); Bromantane (ADK-709); DBL-583; Dichloropane (RTI-111, O-401); Diclofensine (Ro-8-4650); Dieticyclidine; Difemetorex; Difluoropine (O-620); Gacyclidine (GK-11); GBR-12,935; Indatraline (Lu-19-005); Ioflupane (β-CIT-FP); Iometopane (β-CIT, RTI-55); Manifaxine (GW-320,659; Radafaxine (GW-353,162); Tametraline (CP-24, 411); Tesofensine (NS-2330); Troparil (β-CPT; WIN-35, 065-2); Vanoxerine (GBR-12,909); natural chemical such as *Chaenomeles Speciosa* (Flowering Quince); *Psoralea Corylifolia* (Babchi); and the compounds disclosed in WO 2006091697; WO 2001022964, the contents of which are included herein by reference. As methylphenidate indirectly increases dopamine receptor activity, methylphenidate is an indirect dopamine agonist. In some embodiments, (direct or indirect) dopamine agonists that activate dopamine receptor can thus be useful for the purposes of this invention. Dopamine agonists include, but not limited to: amphetamines; methylphenidate; ephedrine; parlodel (bromocriptine); Dostinex (cabergoline); Permax (pergolide); Mirapex and Sifrol (pramipexole); Requip (ropinirole); Apokyn (apomorphine); Neupro (rotigotine). Further dopamine agonists that can be used for the present invention include, but not limited to, the compounds disclosed in U.S. Pat. Nos. 5,212,178; 5,547,958; 4,528,290; 4,552,956; 4,963,569; 5,670,511; EP0,172,697, U.S. Pat. No. 4,698,347, the contents of which are included herein by reference.

Opioid Rectors

There are 3 families of opioid receptors in the brain: Mu (μ), delta (∂) and kappa (κ)◻◻ The caudate-putamen, nucleus accumbens, frontal cortex and ventral midbrain, all of which are intricately involved in the reward and addiction circuitry, are enriched in these receptors (Trigo et al., Drug Alcohol Depend. 2010 May 1; 108(3):183-94). Each receptor is believed to facilitate different aspects of reward circuits via interactions with opioids and neurotransmitters including dopamine and noradrenaline. Activation of the μ opioid receptor (MOPR) and the ∂ opioid receptor (DOPR) is associated with euphoria leading to addiction whereas activation of the κ opioid receptor (KOPR) is associated with dysphoria leading to aversion (Trigo et al., Drug Alcohol Depend. 2010 May 1; 108(3):183-94).

Inhibitors of Opioid Receptors

A number of agents that inhibit opioid receptor are known in the art, and can be used in the compositions and methods described herein. A given agent may inhibit more than one type of opioid receptor. Some inhibitors act on the different opioid receptor types to varying degrees. When inhibition of a specific opioid receptor is desired, a dose of such an inhibitor can be determined by the skilled artisan, that results in increased inhibition of one receptor (e.g., MOPR) over one or more other opioid receptor types (e.g, KOPR and/or DOPR). The use of a combination of one or more opioid receptor inhibitors is also envisioned.

The opioid receptor antagonist may be an opioid analogue, e.g., (CAS number given in parenthesis where appropriate) Naloxone (465-65-6); Naloxonazine (82824-01-9); Cyprodime (118111-54-9); β-Funaltrexamine (72782-05-9); Nalbuphine (20594-83-6); RX 8008M (40994-80-7); SDZ 210-096 (109026-86-0); Clocinnamox (117332-69-1); NIH 10236 (88167-37-7); BU 165 (173321-27-2); BU 164 (173429-52-2); BU 158 (173429-53-3); BU 160 (173429-56-6); BU 161 (173429-57-7); BU 162 (173429-58-8); Buprenorphine (52485-79-7); IOXY (141392-28-1); NPC 168 (115160-07-1); Naloxazone (73674-85-8); N-Methylnaloxonium Iodide (93302-47-7); 3-Methoxynaltrexone Hydrochloride; 7-Benzylidenenaltrexone 129468-28-6); Naltrindole Isothiocyanate (126876-64-0); BNTX (153611-34-8); Naltriben (111555-58-9); Naltrexone (16590-41-3); Nalmefene (55096-26-9); β-Chlornaltrexamine (67025-94-9); Diprenorphine (14357-78-9); nor-Binaltorphimine (105618-27-7); Naltrindole (111555-53-4); or (poly)peptides, e.g., CTAP (103429-32-9); TCTOP (115981-70-9); TCTAP (115981-71-0); CTOP (103429-31-8); Tyr MIF-1 (77133-61-0); CCK-8 (25126-32-3); CG 3703 (90243-66-6); compounds disclosed in Peptide Research 1995, 8(3), 124-37, Proceedings of the National Academy of Sciences of the United States of America (1993), 90(22), 10811-15, Regulatory Peptides (1994), (Suppl. 1), S53-S54; SMS 201-995 (83150-76-9); e-PMTC as disclosed in Medicinal Chemistry Research (1994), 4(4), 245-53; CTP (103335-28-0); TIPP (146369-65-5); ICI-154129 (83420-94-4); ICI-174864 (89352-67-0); or piperidine derivatives, e.g., the compounds disclosed in J. Med. Chem. 1993, 36(20); 2833-41, EP 657428 and EP 506478; or may belong to different structures, such as Quadazocine (71276-43-2); Flumazenil (78755-81-4); BIT (85951-65-1); Dezocine (53648-55-8); Ciramadol (63269-31-8). Ginseng root extract like in Journal of Ethnopharmacology (1994), 42(1), 45-51; Rimcazole (75859-04-0); MR 2266 (56649-76-4); and WIN 44441-3 (71276-44-3).

Compounds which inhibit opioid receptor signalling or down-regulates the expression of opioid receptors in the central nervous system are also suitable for use.

Further opioid receptor antagonists, particularly the pt-receptor, and assays for determining their efficacy in binding to the receptors have been disclosed in e.g., WO 02/098422, U.S. Pat. No. 5,270,328, US 2001/0036951 A, WO 01/42207, WO 01/37785, WO 01/41705, WO 03/101963, WO 2004/005294, WO 2004/014310, WO 2004/038005, and WO 2004/051264, the contents of which are included herein by reference.

Further opioid receptor antagonists which have been disclosed in US 20090325857 comprise Epigallocatechin 3,5-Digallate (37484-73-4), Irigenol Hexaacetate (103652-04-6), Irigenol ex Iris spp (4935-93-7), Berbamine Hydrochloride (5956-76-3), Quercetagetin (90-18-6), Acetylshikonin (24502-78-1), 2',3',4',3,4-Pentahydroxychalcone (484-76-4), beta,beta-Dimethylacryl shikonin (24502-79-2), 2,3-Dimethoxy-5-methyl-1,4-benzoquinone (605-94-7), 2,3-Dimethoxy-5-methylhydroquinone (3066-90-8), 2,3-Dimethoxy-1,4-benzoquinone (3117-02-0), 2,3-Dimethoxyhydroquinone (52643-52-4), Delphinidin chloride (528-53-0), Aureusidin (38216-54-5), Isocembrol (25269-17-4) and Robinetin (490-31-3) without being limited thereto.

Further opioid receptor antagonists which can be used for the purposes of the present invention are disclosed in JP 63290897, U.S. Pat. No. 4,906,655, WO 9302707, CA 2064373, U.S. Pat. Nos. 5,270,220, 5,352,680, WO 9504734, WO 9513071, EP 657428, WO 9606855, WO 9640208, U.S. Pat. No. 5,641,861, WO 9733174, DE 19622866, U.S. Pat. Nos. 5,919,897, 5,948,807, 7,476,679, WO 9945925, WO 2000008027, WO 2001037785, WO 2001041705, WO 2001042207, WO 2001046198, WO 2001068080, US 2001036951, WO 2002053533, WO 2003020277, WO 2003035622, WO 2003035645, WO 2003066050, WO 2003101963, WO 2004014310, WO 2004026305, WO 2004033458, US 2004186135, WO 2004080968, WO 2004080996, US 2004204445, WO 2004091593, WO 2004099194, US 2004254156, WO 2005003131, WO 2005030722 the contents of which are included herein by reference.

Typical μ-opioid receptor antagonists for use herein include, but are not limited to, Naloxone; Levallorphan; Nalorphine; Naloxonazine; piperidine derivatives; Cyprodime; β-Funaltrexamine, Nalbuphine, CTAP, TCTOP, TCTAP, CTOP, Quadazocine, Flumazenil, RX 8008M, SDZ 210-096, Tyr MIF-1, CCK-8, CG 3703, Clocinnamox, peptides such as disclosed in Peptide Research 1995, 8(3), 124-37, Proceedings of the National Academy of Sciences of the United States of America (1993), 90(22), 10811-15, Regulatory Peptides (1994), (Suppl. 1), S53-S54; NIH 10236, BU 165, BU 164, BU 158, BU 160, BU 161, BU 162, Buprenorphine, IOXY, SMS 201-995, e-PMTC as disclosed in Medicinal Chemistry Research (1994), 4(4), 245-53; CTP, BIT, NPC 168, Naloxazone, Dezocine and Ciramadol.

Useful kappa receptor antagonists include, for example, nor-binaltorphimine (norBNI), GNTI (5'-guanidinyl-17-(cyclopropylmethyl)-6,7-dehydro-4,5α-epoxy-3,14-dihydroxy-6,7-2',3'-indolomorphinan), and DIPPA (2-(3,4-dichorophenyl)-N-methyl-N-[(IS)-1-(3-isothiocyanatophenyl)-2-(1-pyrrolidinyl)ethyl]acetamide).

Further kappa receptor antagonists for use herein also include, but not limited to, the ones disclosed in U.S. Pat. Nos. 6,559,159, 7,709,522, EP 1,363,629, U.S. 20020143145, US 20090181999, US20090186873, US 20100035873.

Other inhibitors for use herein include, but are not limited to: N-Methylnaloxonium Iodide, 3-Methoxynaltrexone Hydrochloride; 7-Benzylidenenaltrexone, Ginseng root extract as disclosed in Journal of Ethnopharmacology (1994), 42(1), 45-51; Rimcazole, Naltrindole Isothiocyanate, BNTX, TIPP, Naltriben, Naltrexone, ICI-154129, MR 2266, WIN 44441-3, Nalmefene, β-Chlornaltrexamine, ICI-174864, Diprenorphine, nor-Binaltorphimine and Naltrindole.

The drugs and other compounds described herein, may also be used in the form of physiologically acceptable salts, with inorganic acids, e.g. hydrochlorides, hydrobromides, sulfates, phosphates, or organic acids, e.g. methanesulfonates, p-toluenesulfonates, carbonates, formats, acetates, oxalates, lactates; or as hydrates as appropriate. In addition, the drugs or their salts may be used as racemates or as pure enantiomers, or diastereomers or mixtures thereof. Further, derivatives of these compounds as appropriate, such as esters, amides, nitriles, oximes, imines, hydrazones, ethers, acetals, semiacetals may also find use.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to describe the present invention, in connection with percentages means±1%.

In one respect, the present invention relates to the herein described compositions, methods, and respective component (s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. A pharmaceutical composition comprising a central nervous system stimulant and an opioid receptor antagonist.
2. The pharmaceutical composition of paragraph 1, wherein the opioid receptor antagonist is selected from the group consisting of naltrexone, naloxone, diprenorphine, etorphine, dihydroetorphine, and combinations thereof.
3. The pharmaceutical composition of paragraphs 1-2, wherein the CNS stimulant is selected from the group consisting of methylphenidate, amphetamine, modafinil, and combinations thereof.
4. The pharmaceutical composition of paragraphs 1-3, wherein the CNS stimulant is present in a therapeutic amount and the opioid receptor antagonist is present in an amount for preferred inhibition of the mu opioid receptor.
5. The pharmaceutical composition of paragraphs 1-4, that is formulated for enteral administration.
6. The pharmaceutical composition of paragraph 5, that is formulated for oral administration.
7. The pharmaceutical composition of paragraph 6, that is formulated as a tablet or capsule.
8. The pharmaceutical composition of paragraph 6 or 7, wherein the opioid receptor antagonist is formulated such that when ingested, the opioid receptor antagonist remains intact.

9. A method of reducing or preventing the development of aversion to a CNS stimulant in a subject comprising, administering a therapeutic amount of the neurological stimulant and administering an antagonist of the kappa opioid receptor, to thereby reduce or prevent the development of aversion to the CNS stimulant in the subject.

10. The method of paragraph 9, further comprising selecting a subject at risk for the development of aversion to the CNS stimulant, prior to the administering.

11. The method of paragraphs 9-10, wherein the subject is diagnosed with attention deficit hyperactivity disorder (ADHD), narcolepsy, chronic fatigue syndrome, or depression.

12. A method to decrease the dysphoria associated with the use of therapeutic doses of a CNS nervous system stimulant comprising administering a therapeutic amount of the CNS stimulant and administering a kappa opioid receptor antagonist, to thereby decrease the dysphoria.

13. The method of paragraph 12, further comprising, selecting a subject at risk for the development of dysphoria, prior to administering.

14. A method to decrease the euphoria associated with the use of therapeutic doses of a CNS nervous system stimulant comprising administering a therapeutic amount of the CNS stimulant and administering a mu opioid receptor antagonist, to thereby decrease the euphoria.

15. The method of paragraph 14, further comprising, selecting a subject at risk for the development of euphoria, prior to administering.

16. A method of reducing or preventing the development of addiction to a CNS stimulant in a subject, comprising, administering the CNS stimulant and administering a mu opioid receptor antagonist to thereby reduce or prevent the development of addiction to the CNS stimulant in the subject.

17. The method of paragraph 16, further comprising selecting a subject at risk for the development of addiction to the CNS stimulant, prior to the administering.

18. A method of treating a subject for ADHD, comprising administering a therapeutically effective amount of methylphenidate and administering an opioid receptor antagonist to thereby treat the subject for ADHD.

19. The method of paragraph 18, further comprising, selecting a subject at risk for the development of aversion or addiction to methylphenidate, prior to the administering.

20. The method of paragraphs 9-19 wherein the CNS stimulant is selected from the group consisting of methylphenidate, amphetamine, modafinil, and combinations thereof.

21. The method of paragraphs 9-20, wherein the CNS stimulant results in activation of a dopamine receptor.

22. The method of paragraph 21, wherein the dopamine receptor is selected from the group consisting of D1, D2, D3, D4, D5, and combinations thereof.

23. The method of paragraphs 9-22, wherein the opioid receptor antagonist is selected from the group consisting of naltrexone, naloxone, diprenorphine, etorphine, dihydroetorphine, and combinations thereof.

24. The method of paragraphs 9-23, wherein the administering is oral.

25. The method of paragraphs 9-24, wherein the CNS stimulant and the opioid receptor antagonist are administered in the same pharmaceutical composition.

26. The method of paragraphs 9-24, wherein the CNS stimulant and the opioid receptor antagonist are administered sequentially.

27. The method of paragraphs 9-25, wherein the opioid receptor antagonist is administered in the dosage of from about 50 to about 100 mg.

The invention is further illustrated by the following examples, which should not be construed as further limiting.

EXAMPLES

Example 1

Currently, effective means of preventing stimulant abuse do not exist. The experiments detailed below indicate that a pharmacological approach of combining MPH with naltrexone, an opioid receptor antagonist can serve the purpose of mitigating MPH addiction in a mouse model.

Opioid receptors in the brain fall into 3 subtypes: Mu (µ), delta (∂) and kappa (κ). The caudate-putamen, nucleus accumbens, frontal cortex and ventral midbrain, all of which are intricately involved in the reward and addiction circuitry, are enriched in these receptors[18]. Each receptor is believed to facilitate different aspects of reward circuits via interactions with opioids and neurotransmitters including dopamine[18]. Activation of the µ opioid receptor (MOPR) and the κ opioid receptor (DOPR) is associated with euphoria leading to addiction whereas activation of the κ opioid receptor (KOPR) is associated with dysphoria leading to aversion[18]. Since high doses of MPH can lead to addiction, it was hypothesized that MPH administered at high, supra-therapeutic doses activates MOPR. A key requirement for testing this hypothesis in a mouse model was identifying therapeutic dose of MPH in a mouse. It was established that 0.75 mg/kg MPH administered to adult mice produced serum and brain concentrations of d-methylphenidate (the pharmacologically active isomer) that were equivalent to its serum and brain (estimated) concentrations in ADHD patients taking therapeutic doses of MPH[19]. Therefore, 0.75 mg/kg MPH was considered as therapeutic equivalent dose in mice and 7.5 mg/kg (10 times the therapeutic equivalent dose) as supra-therapeutic or high dose, similar to that used by MPH abusers.

Figure 1B:
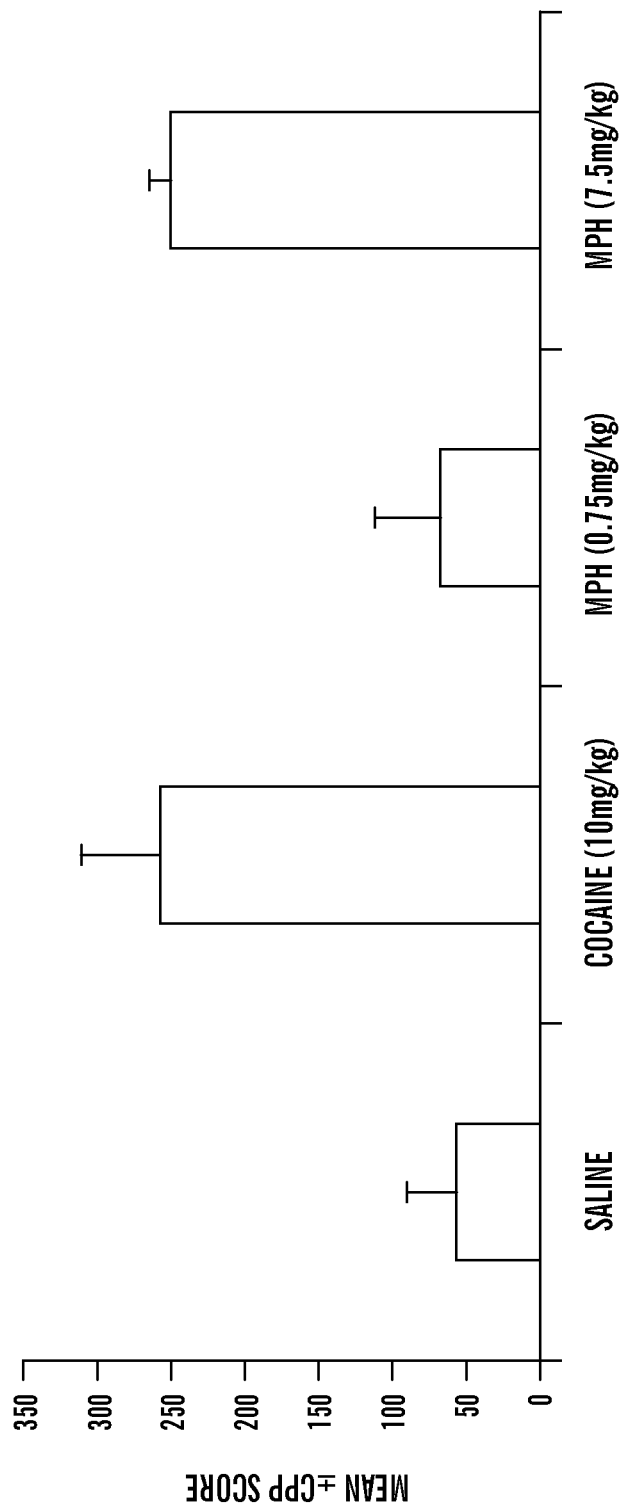

A conditioned place preference (CPP) paradigm was used to establish whether supra-therapeutic doses of MPH (7.5 mg/kg) produced reinforcement in a mouse model. The CPP paradigm consists of training mice to develop an association between drug state and environmental cues. 3 drug stimuli were used: cocaine (10 mg/kg) as a positive control drug because it reliably produces reinforcement, supra-therapeutic MPH (7.5 mg/kg), and therapeutic MPH (0.75 mg/kg). Saline was used as a negative control. The mice exposed to supra-therapeutic dose of MPH or cocaine showed significant place preference, while the mice exposed to low dose MPH or saline did not (FIG. 1A). When the CPP scores were compared among the 4 groups, the high dose MPH (7.5 mg/kg) and cocaine (10 mg/kg) groups showed significantly higher CPP scores compared to the saline and low dose MPH (0.75 mg/kg) groups (FIG. 1B). There was no statistically significant difference in the CPP scores between the high dose MPH and cocaine groups (FIG. 1B). Thus, high dose (but not low dose) MPH was essentially as "addictive" as cocaine.

Figure 2A:
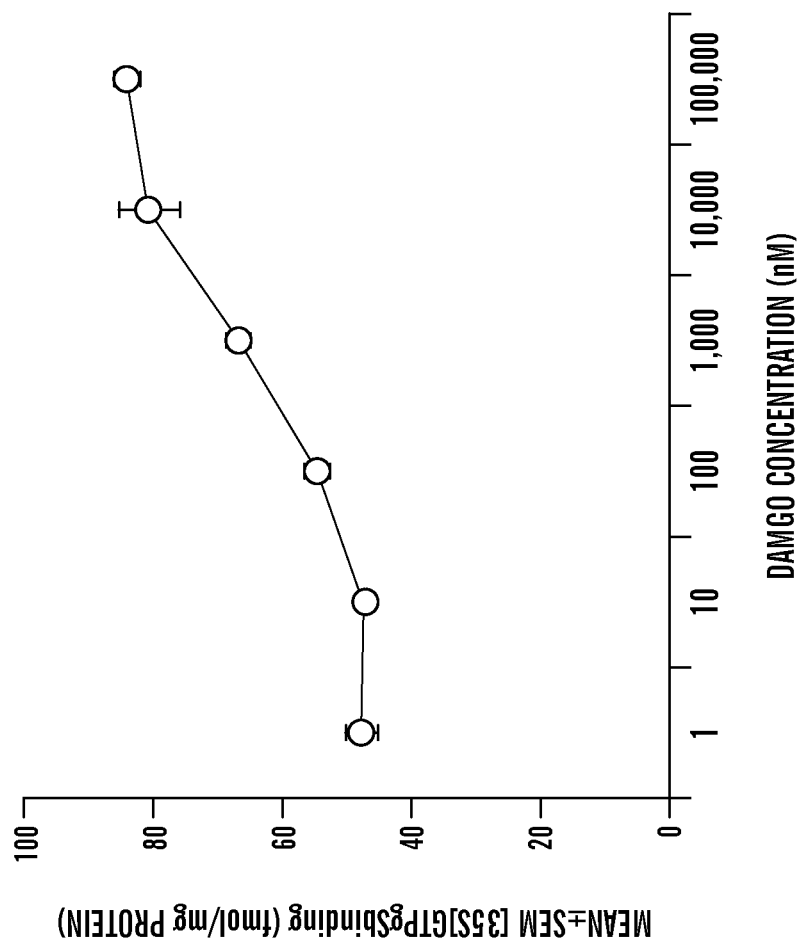
FIG. 2A-2B are graphical representations of experimental results that indicate high supratherapeutic doses of MPH upregulate μ opioid receptor (MOPR) activity in the caudate-putamen and nucleus accumbens. Agonist-stimulated MOPR activity was analyzed using the [$^{35}$S]GTPγS binding assay in membrane preparations of the caudate-putamen and nucleus accumbens from the four groups of mice used in the CPP assay (C).
Figure 2B:
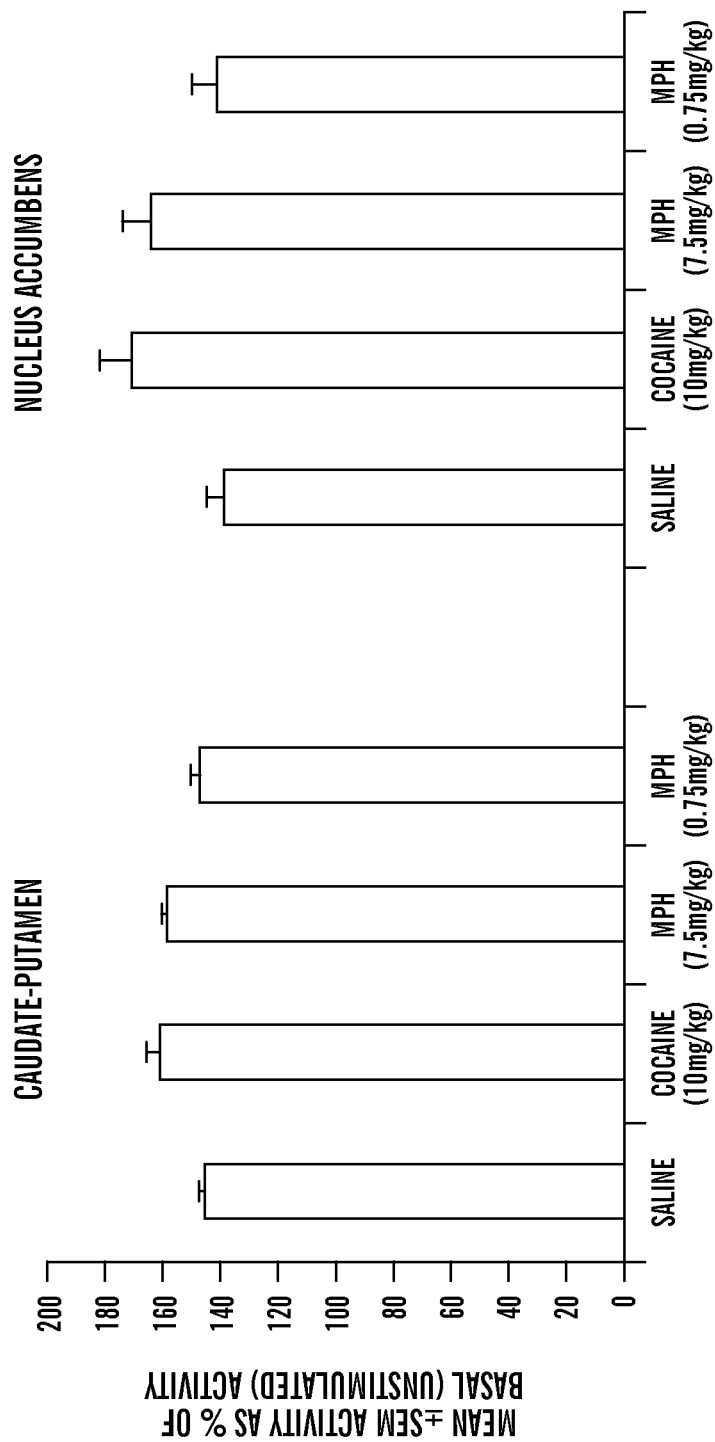

Since upregulation of MOPR is generally associated with rewarding effects—e.g. following cocaine exposure[20,21], whether the 7.5 mg/kg MPH dose that produced CPP also activated MOPR was assessed. The [$^{35}$S]GTPγS binding assays were performed using membrane preparations from the caudate-putamen and nucleus accumbens of mice that had received MPH (0.75 mg/kg or 7.5 mg/kg), cocaine (10 mg/kg) or saline intraperitoneally in the CPP assay. Initial experiments showed that maximal [$^{35}$S]GTPγS binding was achieved at 10 μM DAMGO (FIG. 2A). Therefore, this concentration of DAMGO was used in all the subsequent experiments (FIG. 2B). The basal [$^{35}$S]GTPγS binding (i.e. unstimulated binding) was not significantly different among the different groups. The increase in MOPR agonist DAMGO-stimulated [$^{35}$S]GTPγS binding (compared to the basal levels) in the caudate-putamen (FIG. 2B) and nucleus accumbens (FIG. 2B) of mice exposed to 7.5 mg/kg MPH or cocaine was significantly greater than that in the mice exposed to saline. Low dose (0.75 mg/kg) MPH did not produce significant enhancements in DAMGO-stimulated [$^{35}$S]GTPγS binding.

Figure 3A:
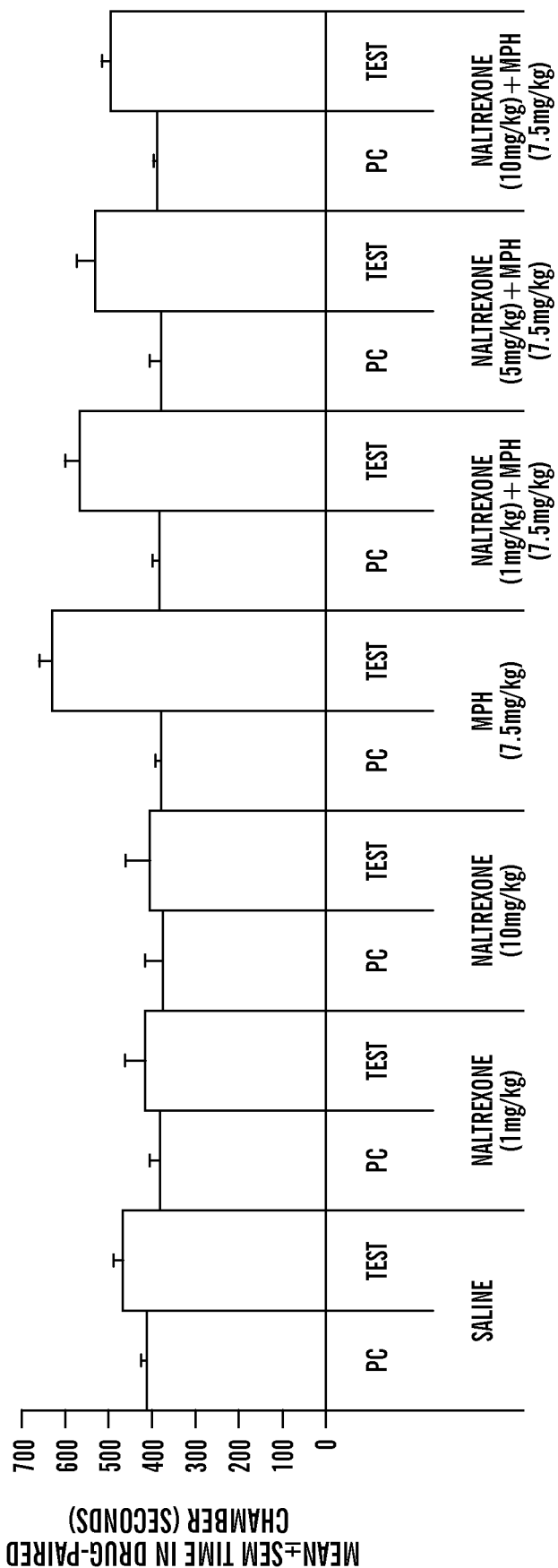
FIG. 3A-3C are graphical representations of experimental results that indicate naltrexone (5 or 10 mg/kg) administration prior to high dose (7.5 mg/kg) methylphenidate (MPH) blocks MPH-induced conditioned place preference (CPP) and MPH-induced activation of the μ opioid receptor (MOPR). CPP using saline (negative control), naltrexone (1, 5 or 10 mg/kg) or MPH (7.5 mg/kg) alone and a combination of MPH and naltrexone (1, 5 or 10 mg/kg) were analyzed.
Figure 3B:
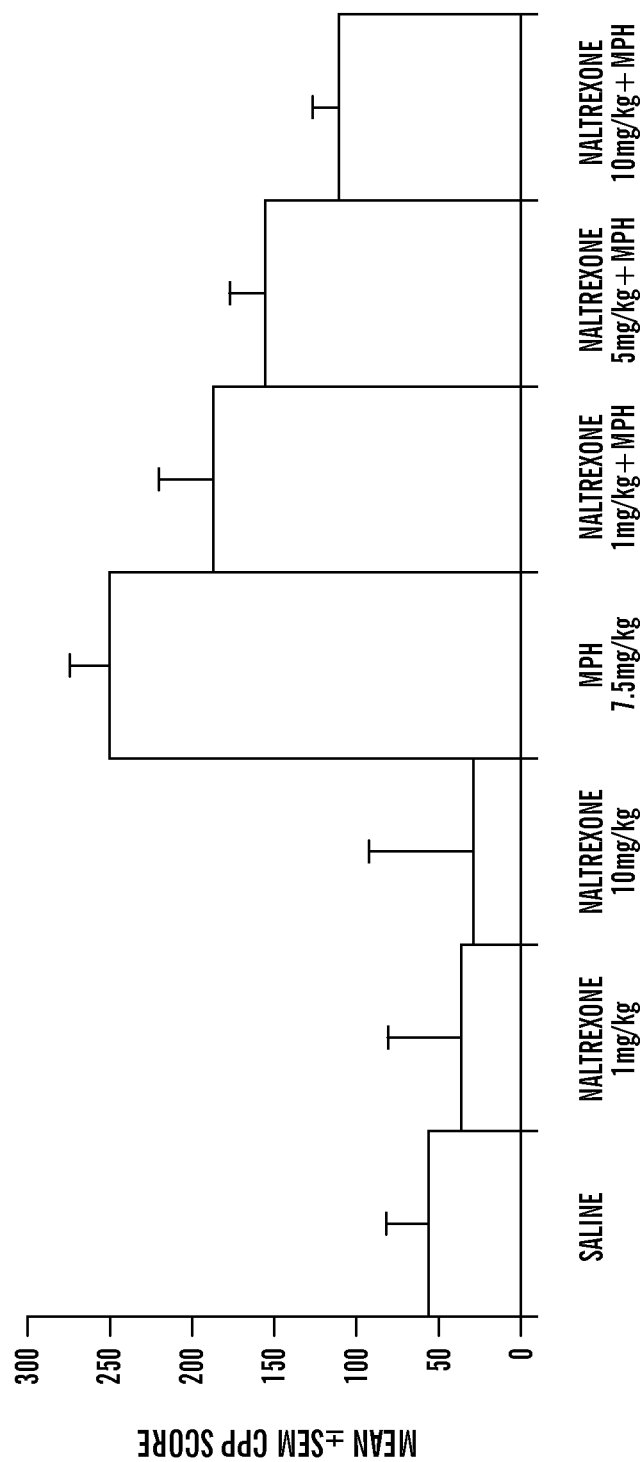

Since the high dose MPH-induced CPP is associated with MOPR activation, it was examined whether an opioid antagonist could attenuate MPH-induced CPP. CPP assays were performed, in which naltrexone, a mixed opioid antagonist, was administered 30 min prior to MPH (7.5 mg/kg). 3 doses of naltrexone (1, 5 or 10 mg/kg) and high dose of MPH (7.5 mg/kg) were used, which reliably induces CPP as well as MOPR activation (FIG. 1). As controls, saline, MPH (7.5 mg/kg) alone or 1 and 10 mg/kg naltrexone alone were used. MPH (7.5 mg/kg) on its own induced CPP (FIG. 3A). However, when naltrexone 5 or 10 mg/kg was administered 30 min prior to MPH, although reinforcement occurred (FIG. 3A), the CPP score under these 2 conditions was significantly lower than the CPP score when MPH was administered alone (FIG. 3B). Naltrexone alone did not affect CPP at 1 or 10 mg/kg dose (FIG. 3A-3B). These data demonstrated that blocking opioid receptors using naltrexone prior to MPH administration can significantly attenuate rewarding effects of MPH.

Figure 3C:
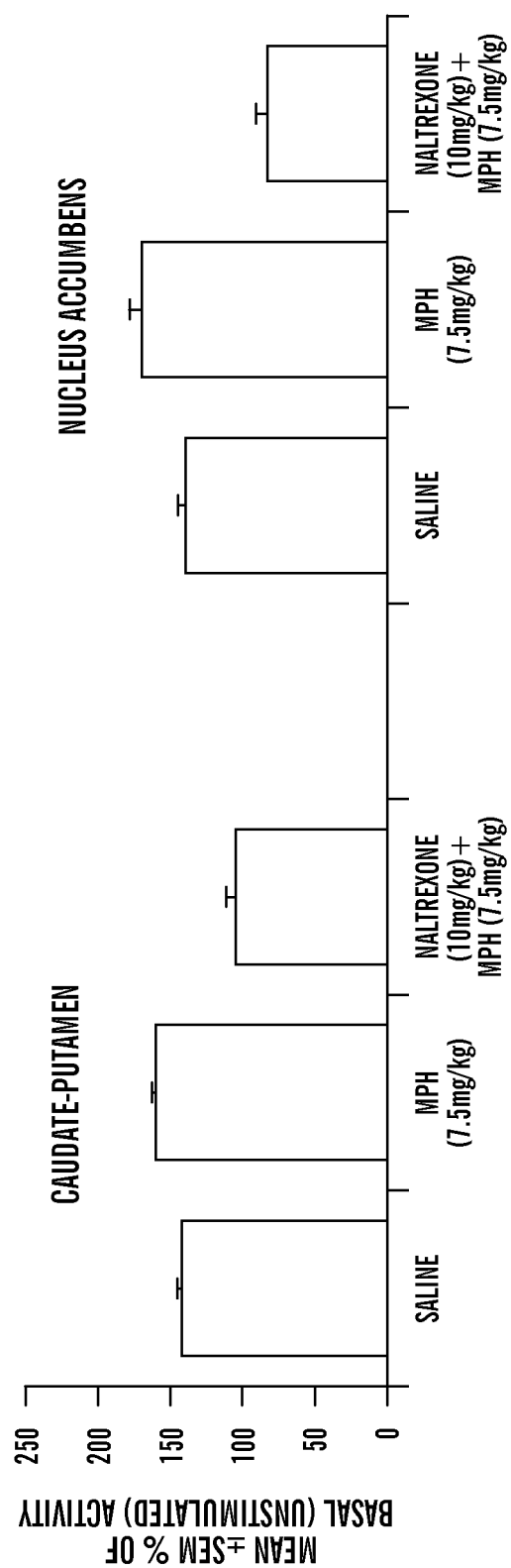

To demonstrate that the naltrexone-induced reduction in the CPP score was indeed due to blockade of the MOPR by naltrexone, MOPR activity following the CPP assay was analyzed. At the end of the CPP assay, samples of the caudate-putamen and nucleus accumbens from each group of mice were collected and MOPR activity was assayed by using [$^{35}$S]GTPγS binding. The basal [$^{35}$S]GTPγS binding was not significantly different among the different groups. However, the MOPR activity was significantly reduced in the caudate-putamen and nucleus accumbens of mice that had received 7.5 mg/kg MPH plus 10 mg/kg naltrexone compared to the mice that had received 7.5 mg/kg MPH alone (FIG. 3C).

Figure 4A:
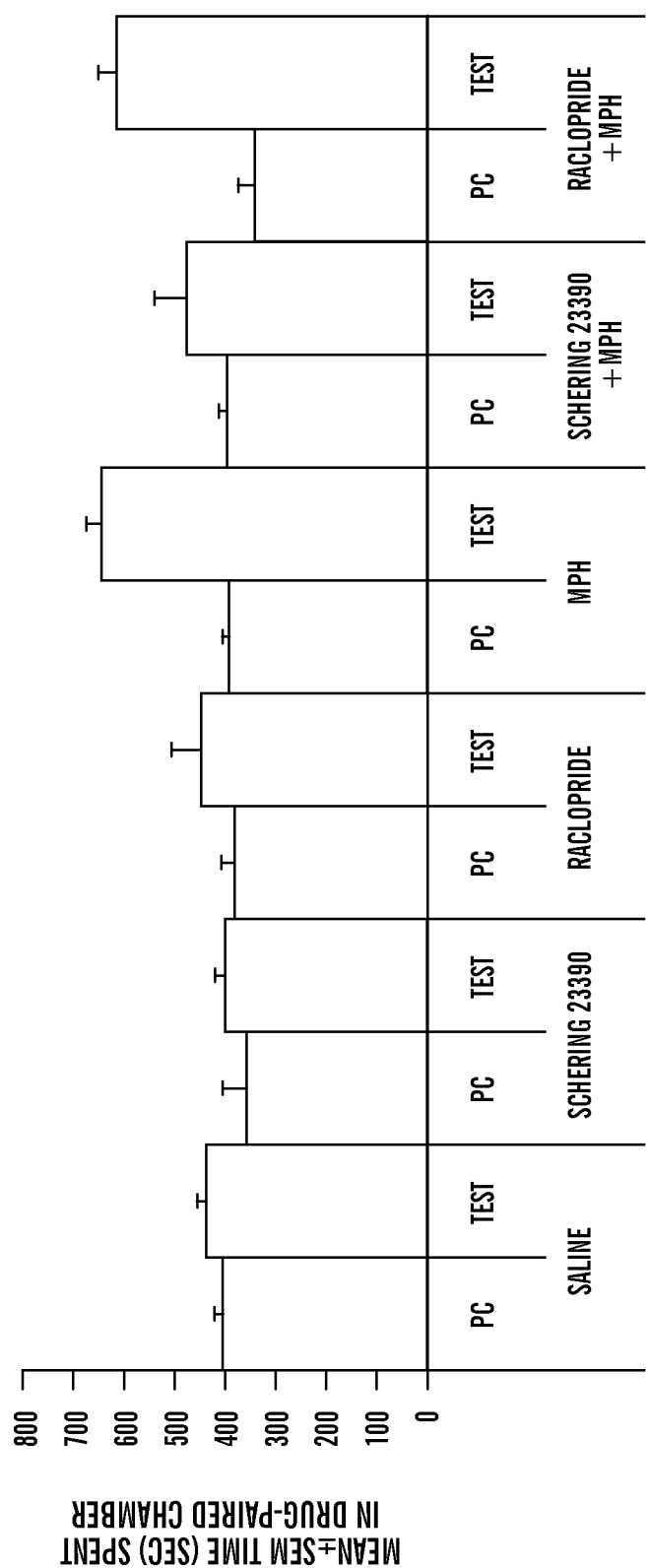
FIG. 4A-4B are graphical representations of experimental results that indicate dopamine D1-receptor antagonist Schering 23390 but not the D2-receptor antagonist raclopride can block high dose (7.5 mg/kg) methylphenidate (MPH) induced conditioned place preference (CPP). CPP assay using saline, Schering 23390 (dose), raclopride (dose) or MPH (7.5 mg/kg) or using a combination of MPH+Schering 23390 and MPH+ raclopride was performed. In the drug combination group, MPH was administered 10 min after the receptor antagonist.
Figure 4B:
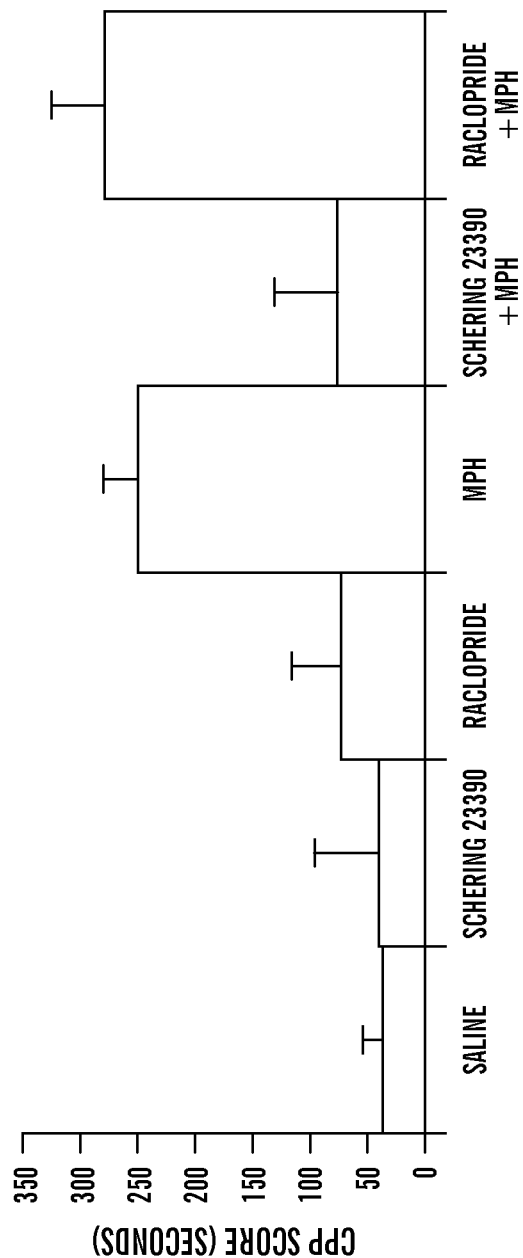

These data demonstrate that supra-therapeutic doses of MPH administered intraperitoneally activate MOPR and produce CPP. Naltrexone administration prior to MPH administration prevents MPH-induced CPP by blocking MOPR. Collectively, these discoveries demonstrate that naltrexone-MPH combination can help mitigate abuse potential of MPH. Earlier reports suggested that in rats, MPH-induced CPP requires dopamine D1-receptor activation[22]. These earlier reports together with the present discovery demonstrate a mechanistic link between MPH, dopamine, MOPR and CPP. To pursue this link further, whether the CPP induced by supra-therapeutic doses of MPH could be blocked by prior exposure to dopamine D1- or D2-receptor antagonists was examined. The D1-receptor antagonist Schering 23390 (0.2 mg/kg) and the D2-receptor antagonist raclopride (0.5 mg/kg) were used. These dosages of the receptor antagonists had been used previously in a rat model of MPH-induced CPP[22]. It was discovered that administration of Schering 23390 but not raclopride 10 min prior to the administration of supra-therapeutic doses of MPH prevented development of CPP (FIG. 4). Since MOPR activation was required for MPH-induced CPP, supra-therapeutic MPH-induced activation of the D1-receptor can lead to activation of MOPR and development of the CPP.

The present discoveries with MPH can be applied to the entire class of stimulant drugs, including amphetamine, as well as analeptics such as modafinil because all of these compounds share a common dopaminergic mode of action and likely affect the MOPR in the same manner as does MPH[26-28]. Stimulant abuse in all sections of the society is on the rise and because these compounds have valuable therapeutic benefits, banning their use is not a practical solution. On the other hand, designing novel pharmacological approaches to rid the compounds of their abuse potential is a viable option. Presented here is the very first evidence that combining MPH and naltrexone can be one such option. The FDA has approved naltrexone for treatment of alcohol and heroin dependence. Therefore, its use for prevention of stimulant and analeptic abuse is feasible and highly timely.

Methods of the Invention

Animals and Materials

Adult C57BL/6 mice were purchased from Charles River Laboratories (Wilmington, Mass.). Only male mice were used. [$^{35}$S]GTPγS (1250 Ci/mmol) was obtained from Perkin-Elmer Life and Analytical Sciences (Boston, Mass.). MPH, cocaine, naltrexone, DAMGO, SCH23390, Raclopride, GDP, GTPγS, and PMSF were purchased from Sigma-Aldrich (St. Louis, Mo.).

Conditioned Place Preference (CPP)

A three-chamber place preference apparatus (Med Associates Inc., St. Albans Vt., USA) was used. The apparatus has two equally sized (16.8×12 cm) preference chambers connected by a central chamber (7.2×12 cm), and is outfitted with sliding guillotine-style doors between each chamber. Photobeams wired to a computer can record animal location (time spent in the chamber). The central chamber has a smooth floor with gray color. Each preference chamber is either white with a mesh floor or black with a bar floor. The CPP procedure included three phases. (1) The pre-conditioning phase was performed on day 1 (two sessions daily, AM and PM). In each preconditioning session, mice were initially placed in the central gray chamber for 2 min and then allowed free access to the white and black chambers for 20 min. The time spent in each chamber was recorded. For the next phase in the assay, the conditioning phase, the non-preferred chamber (i.e. the chamber in which less time was spent) was designated as the drug-paired chamber and the preferred chamber (i.e. the chamber in which more time was spent) was designated as the vehicle-paired chamber. (2) The conditioning phase was carried out on each of days 2 to 6 [two sessions daily, AM and PM one each for vehicle-paired (saline as vehicle) and drug-paired (cocaine or MPH as drugs) sessions]. In the vehicle-paired session mice were injected with saline (i.p.) and placed in the central gray chamber for 2 min (to isolate injection effect to the central chamber) and then confined to the vehicle-paired chamber for 30 min. In the drug-paired session, the mice were given the drug in the central chamber, retained there for 2 min and then confined for 30 min in the drug-paired chamber. At least 4 hours had elapsed between the vehicle-paired and drug-paired sessions; (3) During the test phase, (one session in day 7) the mice were placed in the central gray chamber for 2 min and then given free access to the drug- and saline-paired chambers sides for 20 min. The time spent in each chamber was recorded. The difference between time spent in the drug-paired chamber during the test phase and pre-conditioning phases was calculated as the CPP score.

[$^{35}$S]GTPγS binding

MOPR activity was assayed by using [$^{35}$S]GTPγS binding on membrane preparations using a modification of the previously described method[23]. The mice were sacrificed by cervical dislocation and the brain was dissected rapidly. The caudate-putamen and nucleus accumbens were microdissected and the tissue was homogenized using teflon pistol in Eppendorf tubes (10 strokes) in 300 μl of homogenization buffer containing 25 mM Tris/pH7.4, 5 mM EDTA and 0.1 mM PMSF and kept on ice. Homogenate was diluted to 2.5 ml using the homogenization buffer and centrifuged at ~350,000 g for 30 min. After washing 3 times with 50 mM Tris-HCl/pH7.4, the pellets were re-suspended in 50 mM Tris-HCl/pH7.4 containing 0.32 M sucrose, passed through a 26.5 G needle for 3 times, frozen in dry ice/ethanol and stored in −80° C. until use. DAMGO was used to stimulate MOPR. The membranes (10 μg protein) were incubated in buffer (50 mM HEPES/pH 7.4, 100 mM NaCl, 5 mM $MgCl_2$ and 1 mM EDTA/pH8.0) containing [$^{35}$S]GTPγS (~100,000 dpm, 80 μM) and 100 μM GDP with or without DAMGO in a total volume of 0.5 ml for 60 min at 30° C. Nonspecific binding was defined by incubation in the presence of 10 μM GTPγS, Nonspecific binding was found to be similar in the presence or absence of agonist and was subtracted from total stimulated and total basal binding. Bound and free [$^{35}$S]GTPγS were separated by filtration with GF/B filters under reduced pressure. Radioactivity on filters was determined by liquid scintillation counting. Nonspecific binding was subtracted from total stimulated and basal binding. The basal binding in the caudate putamen was between 45.9±1.9 and 47.5±3.5 fmol/mg protein, while that in the nucleus accumbens was 88.7±7.9 and 92.5±9.3 fmol/mg protein. MOPR activity was reported as % of baseline (unstimulated) activity: [Disintegrations per minute (DPM) with agonist stimulated binding−DPM of nonspecific binding)/(DPM basal (without agonist)−DPM nonspecific)×100. Protein content of membranes was determined by the BCA method of[24] with bovine serum albumin as the standard.

Data Analysis

Differences among the experimental groups were analyzed for statistical significance by using one-way ANOVA. Comparisons between two experimental groups were made by using Newman-Keuls Multiple Comparison Test.

REFERENCES FOR BACKGROUND AND EXAMPLE 1

1. Zuvekas, S. H., Vitiello, B. & Norquist, G. S. Recent trends in stimulant medication use among U.S. children. *Am J Psychiatry* 163, 579-585 (2006).
2. Olfson, M., Marcus, S. C., Weissman, M. M. & Jensen, P. S. National trends in the use of psychotropic medications by children. *J Am Acad Child Adolesc Psychiatry* 41, 514-521 (2002).
3. Brown, R. T., et al. Treatment of attention-deficit/hyperactivity disorder: overview of the evidence. *Pediatrics* 115, e749-757 (2005).
4. Robbins, T. W. ADHD and addiction. *Nat Med* 8, 24-25 (2002).
5. Volkow, N. D. Stimulant medications: how to minimize their reinforcing effects? *Am J Psychiatry* 163, 359-361 (2006).
6. Biederman, J., et al. Is ADHD a risk factor for psychoactive substance use disorders?Findings from a four-year prospective follow-up study. *J Am Acad Child Adolesc Psychiatry* 36, 21-29 (1997).
7. Biederman, J., Wilens, T. E., Mick, E., Faraone, S. V. & Spencer, T. Does attention-deficit hyperactivity disorder impact the developmental course of drug and alcohol abuse and dependence? *Biol Psychiatry* 44, 269-273 (1998).
8. Klein-Schwartz, W. Abuse and toxicity of methylphenidate. *Curr Opin Pediatr* 14, 219-223 (2002).
9. Kuczenski, R. & Segal, D. S. Stimulant actions in rodents: implications for attention-deficit/hyperactivity disorder treatment and potential substance abuse. *Biol Psychiatry* 57, 1391-1396 (2005).
10. Teter, C. J., McCabe, S. E., Boyd, C. J. & Guthrie, S. K. Illicit methylphenidate use in an undergraduate student sample: prevalence and risk factors. *Pharmacotherapy* 23, 609-617 (2003).
11. McCabe, S. E., Teter, C. J., Boyd, C. J. & Guthrie, S. K. Prevalence and correlates of illicit methylphenidate use among 8th, 10th, and 12th grade students in the United States, 2001. *J Adolesc Health* 35, 501-504 (2004).
12. Johanson, C. E. & Schuster, C. R. A choice procedure for drug reinforcers: cocaine and methylphenidate in the rhesus monkey. *J Pharmacol Exp Ther* 193, 676-688 (1975).
13. Bergman, J., Madras, B. K., Johnson, S. E. & Spealman, R. D. Effects of cocaine and related drugs in nonhuman primates. III. Self-administration by squirrel monkeys. *J Pharmacol Exp Ther* 251, 150-155 (1989).
14. Madras, B. K., Fahey, M. A., Bergman, J., Canfield, D. R. & Spealman, R. D. Effects of cocaine and related drugs in nonhuman primates. I. [3H]cocaine binding sites in caudate-putamen. *J Pharmacol Exp Ther* 251, 131-141 (1989).
15. Kuczenski, R. & Segal, D. S. Locomotor effects of acute and repeated threshold doses of amphetamine and methylphenidate: relative roles of dopamine and norepinephrine. *J Pharmacol Exp Ther* 296, 876-883 (2001).
16. Seeman, P. & Madras, B. Methylphenidate elevates resting dopamine which lowers the impulse-triggered release of dopamine: a hypothesis. *Behav Brain Res* 130, 79-83 (2002).
17. Volkow, N. D., Wang, G. J., Fowler, J. S. & Ding, Y. S. Imaging the effects of methylphenidate on brain dopamine: new model on its therapeutic actions for attention-deficit/hyperactivity disorder. *Biol Psychiatry* 57, 1410-1415 (2005).
18. Trigo, J. M., Martin-Garcia, E., Berrendero, F., Robledo, P. & Maldonado, R. The endogenous opioid system: A common substrate in drug addiction. *Drug Alcohol Depend* (2009).
19. Balcioglu, A., et al. Plasma and brain concentrations of oral therapeutic doses of methylphenidate and their impact on brain monoamine content in mice. *Neuropharmacology* 57, 687-693 (2009).
20. Zubieta, J. K., et al. Increased mu opioid receptor binding detected by PET in cocaine-dependent men is associated with cocaine craving. *Nat Med* 2, 1225-1229 (1996).
21. Soderman, A. R. & Unterwald, E. M. Cocaine reward and hyperactivity in the rat: sites of mu opioid receptor modulation. *Neuroscience* 154, 1506-1516 (2008).
22. Meririnne, E., Kankaanpaa, A. & Seppala, T. Rewarding properties of methylphenidate: sensitization by prior exposure to the drug and effects of dopamine D1- and D2-receptor antagonists. *J Pharmacol Exp Ther* 298, 539-550 (2001).
23. Zhu, J., Luo, L. Y., Li, J. G., Chen, C. & Liu-Chen, L. Y. Activation of the cloned human kappa opioid receptor by agonists enhances [35S]GTPgammaS binding to membranes: determination of potencies and efficacies of ligands. *J Pharmacol Exp Ther* 282, 676-684 (1997).

24. Smith, P. K., et al. Measurement of protein using bicinchoninic acid. *Anal Biochem* 150, 76-85 (1985).

Example 2

MPH and amphetamines remain mainstays of treatment in pediatric and adult ADHD (Brown et al., 2005). However, treatment with stimulants is compounded by the dual concerns about their euphoric and dysphoric effects. While the euphoric effects raise concerns about addiction, the dysphoria, irritability and anxiety associated with stimulant treatment are equally taxing to patients and families. Unfortunately, the dysphoric effects do not catch the public's eye as much as the addiction potential. Yet, dysphoric effects are key causes of the serious problem of non-adherence to stimulant treatment regimens. Since the animal model experiment results show that these adverse effects of stimulants can be ascribed to their actions on brain opioid receptors, pharmacological approaches of blocking the opioid receptors can help mitigate these adverse effects. To this end our main goal is to verify the efficacy of the mixed opioid receptor antagonist naltrexone in mitigating MPH-induced euphoria and dysphoria in human volunteers.

Naltrexone does not Affect High Dose MPH-Induced Locomotor Activity

Figure 5:
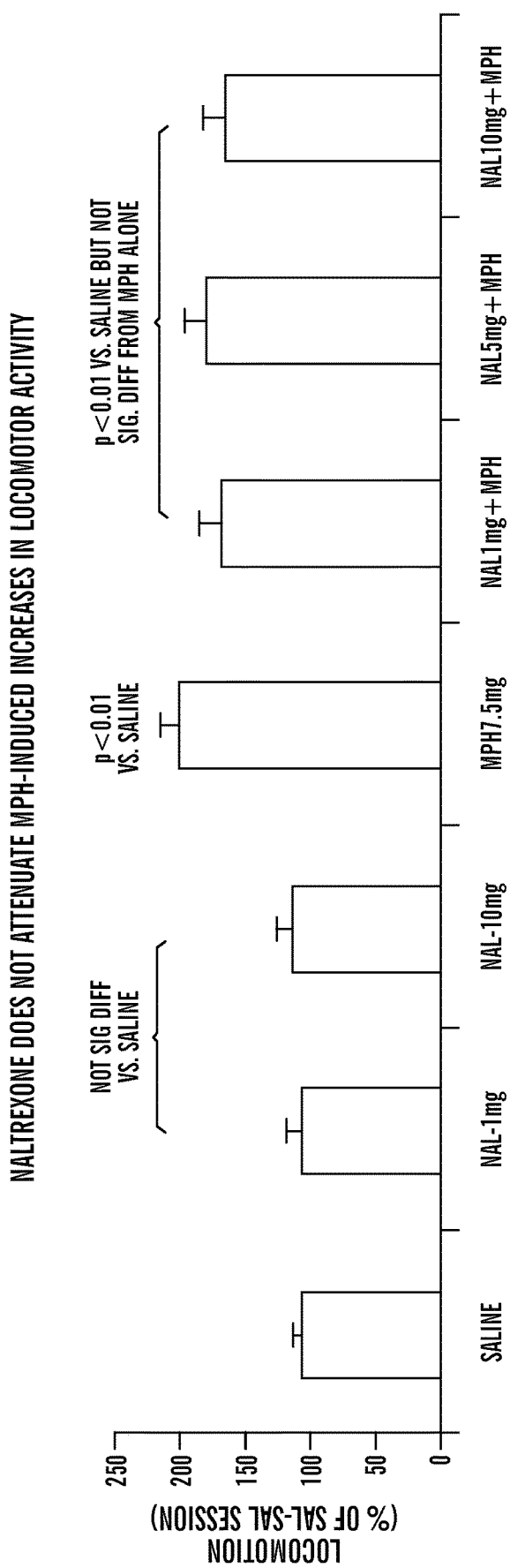
FIG. 5 is a bar graph of experimental results which indicate the effects of saline, naltrexone (1, 5 or 10 mg/kg) alone, MPH (7.5 mg/kg) alone or each dose of naltrexone+MPH on locomotor activity. MPH (7.5 mg/kg) increased locomotor activity significantly. The increase was not affected by co-administration with naltrexone at any of the doses examined. Naltrexone alone did not affect locomotor activity. Data were analyzed by ANOVA. n=11.

During the conditioned place preference assay, locomotor activity, which is a frequently used as a measure of drug sensitization, was also measured. 7.5 mg/kg MPH significantly increased locomotor activity compared to saline (FIG. 5) but 0.75 mg/kg MPH had no significant effect, once again illustrating dose-dependent nature of MPH action. The ability of naltrexone, which blocked high dose MPH-induced place preference, to also block high dose MPH-induced increases in locomotor activity, was examined. 1, 5 or 10 mg/kg naltrexone, 30 min prior to MPH (7.5 mg/kg) was administered. In control groups, saline or naltrexone at each of the doses was administered alone (without MPH). Naltrexone, even at 10 mg/kg, did not block the MPH-induced increases in locomotor activity (FIG. 5). This illustrates dissociation between naltrexone's ability to block MPH-induced place preference versus locomotion. This indicates that euphoric or dysphoric effects of MPH may be antagonized by naltrexone but therapeutic effects can be spared.

Assessing Euphoric and Dysphoric Responses in Human Subjects

The following experiments will extend the studies in mice to humans and verify the efficacy of naltrexone in mitigating euphoria and dysphoria produced by oral doses of MPH in human volunteers. It was previously shown that stimulant-associated euphoria and dysphoria can be adequately assessed in human volunteers (Spencer et al., 2006b; Spencer et al., 2006c). These studies assessed the subjective responses of euphoria (liking) and dysphoria (disliking) of acute oral therapeutic doses of two formulations of MPH in healthy human volunteers using the Drug Rating Questionnaire (DQRS). DQRS has been used in over 27 published studies assessing the abuse liability of stimulants (Jasinski and Henningfield, 1989; Jasinski, 2000; Kollins et al., 2001). Constituent elements of the DQRS scale have been standardized by comparison to responses to known drugs of abuse and validated against observer ratings and physiologic changes (Jasinski and Henningfield, 1989). The first study found that while oral immediate release (IR)-MPH was associated with euphoria (likeability) and dysphoria (dislikeability), a long acting formulation (osmotic controlled-release (OROS)-MPH) was not (Spencer et al., 2006c). In the second study, subjective patterns of likeability and dislikeability as well as pharmacokinetics of OROS-MPH (with a consistently ascending profile) and spheroidal oral drug absorption system (SODAS)-MPH with a more abrupt (50:50) pulsed delivery were compared in 50 adult volunteers that received either drug or placebo in a triple crossover on separate days (Spencer et al., 2006b). Subjective responses were greater on SODAS—than on OROS-MPH. Of subjects on active medication, 38% had at least moderate elevations on the proxy of euphoria (liking scale) and 28% on the proxy of dysphoria (disliking scale). These studies document feasibility and extensive expertise with regard to the studies related to Experiment 3 involving human volunteers.

In summary, preliminary studies show that supra-therapeutic doses of MPH induce place preference (reinforcement or rewarding effect) and that this behavioral adaptation is associated with upregulation of striatal MOPR. Therapeutic doses of MPH neither induce place preference nor striatal MOPR upregulation. Naltrexone, an opioid receptor antagonist attenuates high dose MPH-induced place preference, blocking it completely at the highest dose tested (10 mg/kg naltrexone).

The following experiment will verify that 1) therapeutic equivalent doses of MPH produce place aversion and upregulation of KOPR activity in the mouse brain; 2) Naltrexone blocks therapeutic MPH-induced place aversion in mice; 3) Naltrexone co-administration with long-term therapeutic MPH usage by young adult mice prevents addiction/aversion and opioid receptor signaling; 4) Naltrexone blocks euphoric and dysphoric effects of MPH in human subjects.

Experiment 1

The following experiments will verify that:

a) Supra-therapeutic doses of MPH administered to 90-day old (adult) mice produce MPH conditioned place preference (indirect measure of euphoria leading to addiction) whereas therapeutic doses of MPH produce conditioned place aversion (indirect measure of dysphoria leading to aversion)

b) Co-administration of naltrexone, an opioid receptor antagonist, and supra-therapeutic dose of MPH attenuates MPH-induced conditioned place preference whereas co-administration of naltrexone and therapeutic doses of MPH attenuates MPH-induced conditioned place aversion.

c) MPH-induced conditioned place preference correlates with upregulation of mu or delta opioid receptor activity whereas MPH-induced conditioned place aversion correlates with upregulation of kappa opioid receptor activity in the striatum. Naltrexone-MPH co-administration attenuates both types of changes in opioid receptor activity observed when MPH is administered alone. In each set of studies, activity of all three opioid receptors—mu, delta and kappa—will be analyzed and the receptor activity to behavioral outcome will be compared.

d) Repeated daily exposure to naltrexone plus therapeutic doses of MPH from postnatal day 25 to 60 prevents development of MPH-induced place preference or aversion in young adult mice (60-days old) that would occur if MPH was administered without the naltrexone and prevents changes in opioid receptor activity at P60 that would be produced if MPH was administered alone.

Figure 6A:
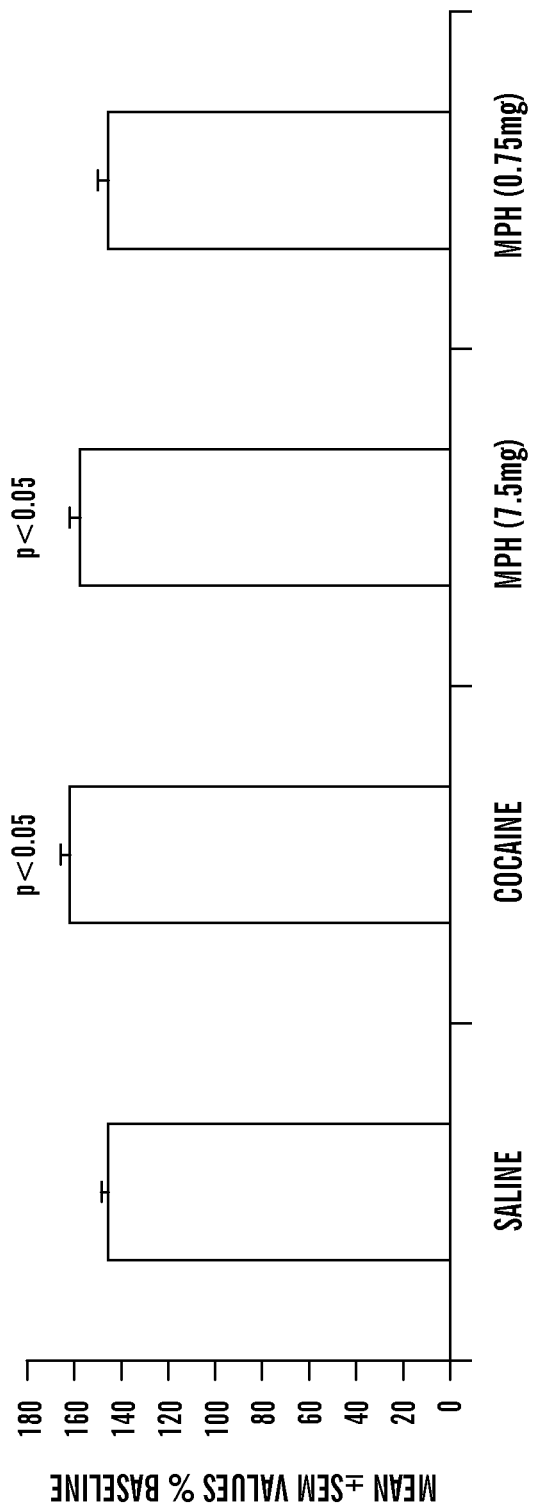
FIG. 6A-6B are bar graphs of experimental results which indicate DAMGO-stimulated [$^{35}$S]GTPγS binding in corpus striatum (FIG. 6A) and nucleus accumbens (FIG. 6B) membrane preparations following intraperitoneal MPH (0.75 or 7.5 mg/kg) or cocaine (10 mg/kg) administration. (t-test; Mean±SEM, **P<0.01, *P<0.05 vs. saline; ++P<0.01, +P<0.05 vs. MPH (0.75).
Figure 6B:
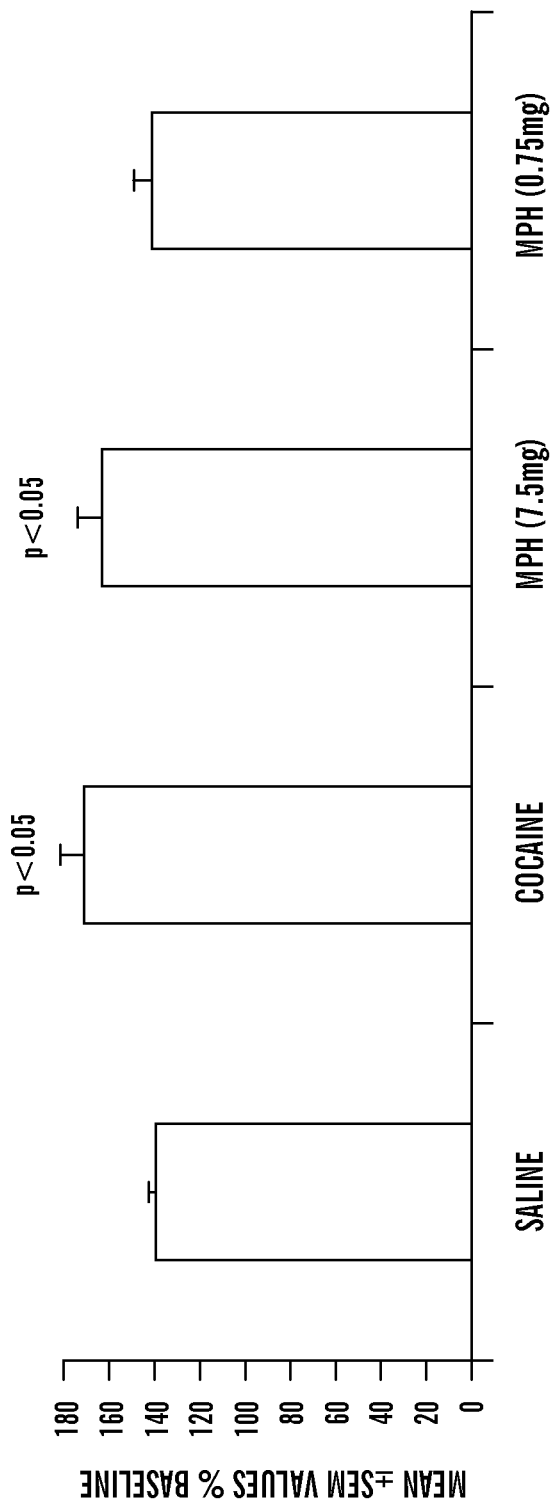

Preliminary analysis showed that supra-therapeutic doses of MPH produce place preference and upregulate MOPR activity whereas therapeutic doses do not. KOPR and delta opioid receptor (DOPR) activities are affected by therapeutic doses. Preliminary data examined MOPR activity only in the striatum and in one case also the nucleus accumbens (FIG. 6). Opioid receptor activity in the frontal cortex, a critical component of the reward and attention circuits and a target of MPH, was not analyzed. In fact, DOPR activity was not examined in any brain region. A comprehensive analysis of all 3 opioid receptors in the caudate-putamen, nucleus accumbens and frontal cortex following therapeutic or supratherapeutic doses of MPH will show that KOPR and delta opioid receptor (DOPR) activities are affected by therapeutic doses. In addition, therapeutic doses of MPH (0.75 mg/kg) produce place aversion and naltrexone can block aversive effects of MPH. Finally, repeated daily exposure to therapeutic doses of MPH beginning in the adolescent period (postnatal day 25) and lasting for 35 days, until young adulthood (postnatal day 60) will be shown to produce changes in MPH-induced conditioned place preference or aversion and in the activity of the 3 types of opioid receptors. In addition, co-administration of naltrexone will be shown to prevent place preference/aversion or changes in opioid receptor activity. In separate studies, the effects of short-term (5 days) MPH administration in these young mice on place preference/aversion and opioid receptor activity will be shown. This is especially relevant to ADHD because MPH treatment for ADHD frequently begins at school age and can last until young adulthood (Safer et al., 1996; Zito et al., 2000). Therefore, the mouse model will establish that MPH administration can lead to euphoric or dysphoric effects in young individuals following short- or long-term MPH administration. Repeated administration of naltrexone+MPH will be shown to prevent MPH-induced addiction or aversion in these developing mice. Postnatal days 25 and 60 in mice represents adolescence and young-adulthood, respectively in humans (Spear, 2000; Andersen et al., 2002b; Andersen et al., 2002a). Mice will not be treated with MPH or naltrexone treatment prior to postnatal day 25 because the stress of weaning (weaning occurs on day 21) could confound the data if drug treatment began before postnatal day 25.

Experimental Methods

C57/Bl6 male mice (Charles River Laboratories, Wilmington, Mass.) in the experiments of Experiments 1, 2 and 3 will be used. The mice will be maintained in the institutional animal facility. The methods of conditioned place preference and opioid receptor activity assays were described in the previous example. The selective MOPR agonist DAMGO, selective KOPR agonist U50,488 and selective DOPR agonist DPDPE ([D-Pen$^{2,5}$]-Enkephalin hydrate) for G-protein coupling assays (all chemicals purchased from Sigma) will be used. MPH and other drugs will be administered twice daily intraperitoneally. Conditioned place aversion employs additional steps compared to conditioned place preference assay. Thus, for conditioned place aversion, an unbiased place conditioning procedure will be used (Tzschentke, 1998). Briefly, to control for apparatus bias, a set of criteria are applied to the preconditioning data. Mice that do not fit the criteria will be excluded from the study. First, any mouse that spends more than 500 seconds of the 1200-second test period in the central chamber will be excluded. Of the mice that qualify, the time spent in the central chamber will be subtracted from 1200 (the total test time), and divided by two to give a "half-time" (equal to the amount of time the mouse would spend in each chamber, saline-paired and drug-paired, if it had absolutely no preference). The half-time will be multiplied by 0.2 and this value will be added or subtracted to the half time to give a range of allowable time a mouse can spend in either chamber. If the time spent in one chamber exceeds the upper or lower limits of the range then the mouse is assumed to have an apparatus bias and will be removed from the study. Mice will be then randomly assigned to a given treatment group. The remainder of the procedure will be the same as that described for conditioned place preference. The data will be analyzed by ANOVA. Differences between two given experimental groups will be tested for significance by using t-test.

Expected Outcomes and Alternative Strategy

Based on the literature (Kuczenski and Segal, 2001; Meririnne et al., 2001; Kuczenski and Segal, 2002; Brandon et al., 2003; Chase et al., 2005) it is expected that adult mice administered 0.75 mg/kg MPH for 5 days (as part of the place preference/aversion paradigm) will show place aversion as opposed to the place preference produced by 7.5 mg/kg dose. It is expected that 0.75 mg/kg MPH will upregulate KOPR activity in the caudate-putamen, nucleus accumbens and frontal cortex. MPH (0.75 mg/kg) administration for 5 or 35 days beginning at postnatal day 25 is also expected to produce place aversion and upregulate KOPR activity, based on reports cited above. DOPR activity will be expected to parallel MOPR activity and KOPR activity will be the opposite. 7.5 mg/kg MPH administered to 25-day old mice for 5 days will be expected to produce similar effects as those in 90-day old mice, i.e. place preference and MOPR upregulation. Co-administration of naltrexone and MPH is expected to block MPH-induced aversion. Since MOPR, KOPR and DOPR activity will be measured in each experiment, the ratio between activities of euphoria- and dysphoria-associated receptors, i.e. (MOPR+DOPR)-to-KOPR in addition to individual receptor activity will be analyzed. It is possible, that individual receptor activity will not show significant changes but the ratio will. From the functional perspective, changes in the ratio will suggest a tilt of the balance in favor of euphoria- or dysphoria-associated receptors.

It is recognized that interpretation of data could pose challenges if receptor activities did not change coherently in the 3 brain regions to be examined. That is, a given receptor may be upregulated in the nucleus accumbens but down-regulated in the striatum or frontal cortex. MPH and opioids affect diverse pathways ranging from attention to analgesia. Therefore, the changes in receptor activities produced by the drugs could also be diverse. To the extent possible, regional differences in receptor activity will be correlated with behavioral effects observed in Experiment 2. The motivation for proposing this analysis is that low doses of MPH selectively affect neurotransmitter levels in the frontal cortex (Gerasimov et al., 2000; Kuczenski and Segal, 2002; Balcioglu et al., 2009). Amphetamine (2.5 mg/kg; s.c.) modulates KOPR signaling in the nucleus accumbens in a region-specific manner (Xia et al., 2007). Thus, therapeutic effects of MPH likely require region-specific changes in neurotransmitters. Therefore, 0.75 mg/kg MPH may affect opioid receptor activity selectively in the frontal cortex. If therapeutic doses of MPH+naltrexone altered opioid receptor activities in regions other than frontal cortex, it may be reflected in changes in attention in Experiment 2.

Alternative doses of MPH for use will be a) 1.5 mg/kg of MPH, or b) 0.75 or 1.5 mg/kg MPH administered for a longer period, 15 days. Finally, naltrexone may not block MPH-induced place aversion even at 10 mg/kg (the dose that blocks MPH place preference). Alternative doses of naltrexone for use will be 15 or 20 mg/kg naltrexone. In addition, a selective KOPR antagonist bupronorphine will be used in place of naltrexone. Since place aversion is mediated via KOPR, and since naltrexone blocks all 3 opioid receptors, using a selective KOPR antagonist may be more effective in blocking the aversion. It is important to note that MPH intolerance is typically observed in human subjects (Spencer et al., 2006a; Spencer et al., 2006b).

Experiment 2

The following experiment will show that naltrexone-MPH co-administration does not adversely influence the effects of MPH on attentional mechanisms in a 2-choice serial reaction time test. The effects of MPH alone versus naltrexone+MPH on operant extinction learning will also be compared. Each of the analyses will be performed following twice daily, short-term (5 days) or long-term (35 days) drug administration.

0.75 mg/kg MPH plus 5 or 10 mg/kg naltrexone (these doses were effective in Preliminary studies) will be used. Behavioral analyses will be performed in collaboration with and under the direct supervision of Dr. Jean-Cosme Dodart. The principal assay will be the 2-CSRT assay recently developed in Dr. Dodart's lab (Dillon et al., 2009). This is a novel attention task that overcomes some of the limitations of the other attentional task used in rodents, the 5-CSRT task. The 5-CSRT requires an average training period of 3-4 months for normal rodents (i.e. rats or mice) to reach a 70-80% criterion level of performance. The 2-CSRT can be performed in 8-10 days. Thus, The 2-CSRT does not involve extensive training period, multiple attentional tests, nor potential confounds across different behavioral endpoints. In order to optimize the behavioral protocol, visual discrimination learning will be first compared under different operant training conditions. Then the mice will be tested in a novel mixed-trial attention paradigm combining four different stimulus durations within a single session (0.5, 1, 2, or 10 s). The stimulus durations used during attention testing will provide within session controls, such that chance level performance will occur at the shortest stimulus duration (0.5 s) and optimal attention-independent performance at the longest stimulus duration (10 s). The attentional demand at the longest stimulus duration should be minimal; therefore performance deficits during these trials might indicate either motivational and/or motor alterations.

The 2-CSRT testing apparatus is a standard rat operant chamber (Med Associates, St Albans, Vt.). A pellet receptacle will be placed in the center of one end-wall with a small yellow stimulus light located directly overhead. Two retractable lever-press devices will be located on each side of the end-wall opposite to the pellet receptacle. A large stimulus light is located directly above each lever to operate as a direct cue during the discrimination and attention tasks. The visual discrimination learning and attention procedures are described in detail in a recent publication from Dr. Dodart's lab (Dillon et al., 2009).

The test includes 4 phases: (1) A single habituation session: The food-restricted mice are exposed to the operant chamber for 45 min without access to the operant levers but receive 24 exposures to a 1-s receptacle-light stimulus with an inter-trial interval (ITI) of 120 s. The presentation of the receptacle-light stimulus coincides with the delivery of a 20-mg food pellet; (2) 2-daily shaping sessions: Only one lever (left or right) is available indefinitely concurrently with random light presentation until the subject makes a response. Following each response the lever is retracted, food receptacle light turned on, and a single 20-mg food pellet is delivered. Each additional trial begins 10 s following the retrieval of the food reward. Shaping sessions last for a maximum of 30 min or 60 trials; (3) 8-daily discrimination training sessions: Each daily session includes 80 trials beginning with the presentation of both levers accompanied by a cued stimulus light directly above one of the levers. Light-lever is randomly paired and counterbalanced across trials. Animals have to press the lever signaled by the light stimulus to obtain food reward. The stimulus light remains illuminated until a lever-press is made or for a maximum duration of 30 s. Following a correct response levers are retracted, a reward is delivered into the receptacle and the receptacle light remains turned on until the pellet is retrieved. The animal visits the receptacle in a 10-s ITI during which the house light remains turned on. Following an incorrect response, levers are retracted, no reward is delivered, and the house light is switched off for a 30-s ITI. An omission is recorded when an animal does not respond within 30 s after the presentation of the levers. Following an omission both levers are retracted and the house light is turned off for a 30-s ITI. (4) 3-daily attention sessions: These follow an identical protocol to the discrimination procedure with the exception that the duration of the light stimulus is reduced to 0.5, 1, 2, or 10 s. whereas animals still have 30 s to respond before an omission is recorded. At each stimulus duration, 20 trials are performed within a session (45 min maximum, 80 trials total), and stimulus durations and lever-stimulus pairings are distributed randomly and counterbalanced across trials. Attention sessions last for ~35 min in run time. In this paradigm, significant increases in errors in the 0.5, 1, and/or 2 s stimulus durations represents attention deficit whereas increased errors in the 10 s duration likely represents changes in motivation and/or motor activity (Dillon et al., 2009).

In separate cohorts of mice from each experimental group (and controls) mentioned above, operant extinction learning performance will be assessed. The mice will be trained in a lever-press task under continuous reinforcement and extinction learning performance will be assessed. This paradigm provides behavioral measures of response inhibition and frustration (Dillon et al., 2008), which is associated with attention deficits caused, for example by prenatal nicotine exposure in children (Huijbregts et al., 2008). This test is considered to be a good indicator of the "therapeutic" benefits of MPH and whether naltrexone produces adverse effects on the potency of MPH in this test. Prior to training, food-restricted mice will be exposed to the operant chambers (Med Associates, St. Albans, Vt.) for 45 min without access to the operant lever. For this paradigm, operant chambers are configured with one pellet receptacle placed in the center of one end-wall (with a small yellow stimulus light located directly above the receptacle) and one lever placed adjacent to the receptacle (this lever is available to the animal at all time during acquisition and extinction sessions. During the habituation session, the mice receive 20 exposures to a 1-s light stimulus with an inter-trial interval of 120 s. Each stimulus light display is paired with the delivery of a food pellet. Training begins 24 h following habituation and consists of daily 30-min sessions under continuous reinforcement (FR1 schedule). Extinction training begins 24 h after the final training session. Daily extinction sessions are conducted over 3 days under similar conditions as during acquisition, with the exception that food pellets are no longer delivered after a lever press. Lever presses followed by a head entry into the food cup within 30 s are scored as chained responses. Lever presses followed by another lever press (without a visit to the receptacle) are scored as unchained responses. Total lever presses, chained and unchained responses are collected automatically by the MED-PC IV software. Data from each behavioral assay will be analyzed by ANOVA.

In each set of studies, the drug administration will occur 1 hr prior to the test session. This time-frame is consistent with previous data (Balcioglu et al., 2009), which show that although clinically relevant serum levels of D-MPH (6-10 ng/ml) are reached within 15 min of administration at 0.75 mg/kg dose, brain levels remain high for ~30 min and region-specific and monoamine species-specific increases in frontal cortical dopamine levels occur ~60 min after the MPH administration. Therefore, MPH administration 1 hr prior to the behavioral test seems reasonable. However, if a single administration does not produce significant effects on attentional mechanisms, repeated dosing will be used. The entire test paradigm will be repeated in a new cohort of mice prior to and following naltrexone (5 or 10 mg/kg) plus MPH (0.75/mg/kg) administration. Separate set of studies will be performed to determine if developmental MPH or naltrexone+MPH administration produces different effects on attention by administering MPH (0.75 mg/kg) or naltrexone (5 or 10 mg/kg)+MPH (0.75 mg/kg) daily for 35 days beginning at postnatal day 25. The 2-CSRT testing for this group of mice will begin at postnatal day 60.

Expected Outcomes and Alternative Strategy

The expectation of the study is that therapeutic doses of MPH (0.75 mg/kg) will improve attention and reduce frustration and that co-administration of naltrexone (10 mg/kg) and MPH will not influence the effects of MPH alone. Alternative doses of MPH for use will be 1.5 mg/kg. It is previously shown that 0.5 mg/kg MPH increased accuracy in rats in a 5-CSRT assay (Paine et al., 2007). Therefore, 0.75 mg/kg MPH is expected to produce beneficial effects in mice in the 2-CSRT. The effects of co-administration of selective KOPR and DOPR antagonists mentioned in Experiment 1 will also be tested to determine which receptor contributes to any outcomes. Preliminary findings show that at least 5 mg/kg naltrexone is needed to block reinforcing properties of 7.5 mg/kg MPH. Higher doses of naltrexone will also be used to block MPH-induced aversion. Suitable doses are expected to be between 10 and 15 mg/kg.

Experiment 3

The following experiment will show that MPH-induced dysphoria and euphoria in humans can be attenuated by co-administration of the non-specific opioid receptor antagonist naltrexone.

In this Experiment the safety and efficacy of the mixed opiate antagonist naltrexone in mitigating euphoria and dysphoria in human volunteers exposed to therapeutic oral doses of MPH will be verified. This therapeutic approach will have enormous clinical and public health relevance by minimizing the two equally taxing problems associated with stimulant treatments, euphoria and dysphoria. Naltrexone is uniquely suited for this purpose because it antagonizes both MOPR and KOPR and has the potential to mitigate both MPH-induced euphoria and dysphoria. Moreover, it is commercially available and FDA approved for the treatment of alcoholism with available data on dosing, safety and efficacy for this indication. The approach is feasible since stimulant associated feeling states of euphoria and dysphoria can be reliably assessed in humans (Spencer et al., 2006c). Subjective drug experience, especially euphoria, is thought to be an indicator of risk of abuse (Jasinski and Henningfield, 1989; Jasinski, 2000; Kollins et al., 2001) and dysphoria is thought to be a major determinant of tolerability and adherence with treatment regimen in clinical practice. Subjective responses to oral MPH were reported in 18 (72%) of 25 studies that evaluated detection/likeability (Kollins et al., 2001). Likewise the large extent of clinical trials literature documents the frequent occurrence of dysphoric effects in clinical populations that adversely impact tolerability and eventually compliance with stimulant treatment.

100 healthy volunteers between 18 and 55 years will be enrolled. All subjects will have a complete medical and psychiatric history and physical examination before imaging. None will have any DSM-IV axis I disorders including ADHD as well as current or past drug or alcohol abuse. In addition none will have a history of exposure to psychotropic medicines (including stimulants). In females, inquiry about the subject's current reproductive status will be also made. In addition, all subjects will have an ECG, full blood count, blood chemistries and urinalysis (including drug screen and, in females, a pregnancy test). Two screening visits will allow for the determination of the appropriateness of each subject's inclusion in the study. Potential subjects will provide written informed consent prior to initiation of any study related procedures or questions. At the first visit, all subjects will undergo the following procedures: clinical assessments, complete medical history, physical examination, vital signs, urine pregnancy test for females of childbearing potential, electrocardiogram, clinical lab tests including urinalysis and urine drug test. At the second visit, subjects will be administered one dose of immediate-release (IR) methylphenidate (60 mg) and one dose of placebo during the visit to confirm that they have a subjective response to MPH. Subjects will be blinded to the dose they are receiving. After administration of the dose subjects will be asked Questions 2 and 3 (Do you like the drug effect? Do you dislike the drug effect) of the Drug Rating Questionnaire (DRQ-S) hourly for up to 4 hours. At least one response out of 5, at one time point after taking the IR-dose is required for participation in the randomized part of the study.

Based on findings from previous studies, of the 100 screened subjects, 28 are expected to have at least moderately elevated ratings for liking scale, 18 to have at least moderately elevated ratings for disliking and 10 additional subjects would have at least moderately elevated ratings for both. Thus these 56 individuals—38 of those responding as liking and 28 for those responding to disliking—would be randomized. Randomized subjects will receive MPH±naltrexone. Naltrexone doses will be blinded by the formulation of identical placebo capsules. All subjects will receive both conditions (MPH plus naltrexone, MPH without naltrexone) in a crossover design on separate days. The order of assignment of medication will be randomized by the pharmacy. Subjects and clinicians will be blind to medication assignment. The dose of MPH will be 60 mg (Spencer et al., 2006b; Spencer et al., 2006c), the dose of naltrexone will be 50 mg (Jayaram-Lindstrom et al., 2004). These doses are consistent with current FDA-approved guidelines. Venous blood will be drawn for quantification of peak plasma concentration of d-MPH and naltrexone. Each study day subjects will receive both doses of medication [MPH plus naltrexone, MPH without naltrexone (placebo)] in the morning and then complete hourly DQRS. The DQRS is a subjective drug effects scale that has been used to measure a factor in abuse liability. The liking question assesses potential for euphoria, disliking measures dysphoria. Constituent elements of the scale have been standardized by comparison to responses to known drugs of abuse and validated against observer ratings and physiologic changes (Jasinski and Henningfield, 1989). This measure and related scales have been used in over 27 published studies assessing the abuse liability of methylphenidate (Jasinski and Henningfield, 1989; Jasinski, 2000; Kollins et al., 2001). Subjects will complete the DQRS hourly for 10 hours on each of the study days (Spencer et al., 2006c).

Categorical data will be analyzed with chi-square tests, continuous parametric data with unpaired t or F tests, and nonparametric data with the rank sum test. Associations between continuous variables will be evaluated by Pearson's product-moment correlation. Multiple comparisons will be controlled by using Holm's sequential Bonferroni method. In computing Holm's test, Nyholt's method (Nyholt, 2004) will be used to adjust the total number of tests that were assumed.

Expected Findings, Interpretation and Alternative Approaches

It is expected that subjects receiving MPH plus placebo will have significantly more severe ratings than those on MPH plus naltrexone on all three DQRS scales including Feeling, Liking and Disliking. Randomized subjects will have already been screened for a subjective response (Feeling) to oral MPH. Naltrexone is expected to attenuate both the euphoric and dysphoric reactions associated with MPH. Successful outcomes are indicated strongly from results of an earlier study that used an identical paradigm to test whether naltrexone can mitigate the subjective effects (liking or disliking) of amphetamine in healthy human volunteers (Jayaram-Lindstrom et al., 2004). An alternative dose of 100 mg naltrexone will be used. It is also important to note that the subjective feelings analyzed here are not necessarily expected to directly correlate with the mouse data. In the human studies, the drugs are administered once whereas in the conditioned place preference/aversion assays in mice the drugs are administered repeatedly. Finally, long-acting (osmotic release) produces less euphoria/dysphoria than the short-acting (immediate-release) MPH (Spencer et al., 2006c). However, the short-acting MPH is less expensive than the long acting preparation and it is used extensively. Therefore, designing ways to make the short-acting MPH free from addiction/aversion potential is a highly significant and timely approach.

An effective dose range of naltrexone for all the studies is expected to be 5 to 15 mg/kg. However, higher and lower doses are also envisioned.

REFERENCES FOR EXAMPLE 2

1. Andersen S L, Thompson A P, Krenzel E, Teicher M H (2002a) Pubertal changes in gonadal hormones do not underlie adolescent dopamine receptor overproduction. Psychoneuroendocrinology 27:683-691.
2. Andersen S L, Arvanitogiannis A, Pliakas A M, LeBlanc C, Carlezon W A, Jr. (2002b) Altered responsiveness to cocaine in rats exposed to methylphenidate during development. Nat Neurosci 5:13-14.
3. Araki K Y, Sims J R, Bhide P G (2007) Dopamine receptor mRNA and protein expression in the mouse corpus striatum and cerebral cortex during pre- and postnatal development. Brain Res 1156:31-45.
4. Araki K Y, Fujimura S, MacDonald M E, Bhide P G (2006) Characterization of mouse striatal precursor cell lines expressing functional dopamine receptors. Dev Neurosci 28:518-527.
5. Balcioglu A, Ren J Q, McCarthy D, Spencer T J, Biederman J, Bhide P G (2009) Plasma and brain concentrations of oral therapeutic doses of methylphenidate and their impact on brain monoamine content in mice. Neuropharmacology 57:687-693.
6. Bergman J, Madras B K, Johnson S E, Spealman R D (1989) Effects of cocaine and related drugs in nonhuman primates. III. Self-administration by squirrel monkeys. J Pharmacol Exp Ther 251:150-155.
7. Biederman J, Wilens T E, Mick E, Faraone S V, Spencer T (1998) Does attention-deficit hyperactivity disorder impact the developmental course of drug and alcohol abuse and dependence? Biol Psychiatry 44:269-273.
8. Biederman J, Wilens T, Mick E, Faraone S V, Weber W, Curtis S, Thornell A, Pfister K, Jetton J G, Soriano J (1997) Is ADHD a risk factor for psychoactive substance use disorders? Findings from a four-year prospective follow-up study. J Am Acad Child Adolesc Psychiatry 36:21-29.
9. Blockmans D, Persoons P, Van Houdenhove B, Bobbaers H (2006) Does methylphenidate reduce the symptoms of chronic fatigue syndrome? Am J Med 119:167 e123-130.
10. Brandon C L, Marinelli M, White F J (2003) Adolescent exposure to methylphenidate alters the activity of rat midbrain dopamine neurons. Biol Psychiatry 54:1338-1344.
11. Brenhouse H C, Napierata L, Kussmaul L, Leussis M, Andersen S L (2009) Juvenile methylphenidate exposure and factors that influence incentive processing. Dev Neurosci 31:95-106.
12. Brown R T, Amler R W, Freeman W S, Perrin J M, Stein M T, Feldman H M, Pierce K, Wolraich M L (2005) Treatment of attention-deficit/hyperactivity disorder: overview of the evidence. Pediatrics 115:e749-757.
13. Bruera E, Driver L, Barnes E A, Willey J, Shen L, Palmer J L, Escalante C (2003) Patient-Controlled Methylphenidate for the Management of Fatigue in Patients With Advanced Cancer: A Preliminary Report. J Clin Oncol 21:4439-4443.
14. Caldwell J A, Caldwell J L, Crowley J S, Jones H D (1995) Sustaining helicopter pilot performance with Dexedrine during periods of sleep deprivation. Aviat Space Environ Med 66:930-937.
15. Cenci M A, Lee C S, Bj"rklund A (1998) L-DOPA-induced dyskinesia in the rat is associated with striatal overexpression of prodynorphin- and glutamic acid decarboxylase mRNA. EurJNeurosci 10:2694-2706.
16. Chase T D, Carrey N, Brown R E, Wilkinson M (2005) Methylphenidate differentially regulates c-fos and fosB expression in the developing rat striatum. Brain Res Dev Brain Res 157:181-191.
17. Cornum R, Caldwell J, Cornum K (1997) Stimulant use in extended flight operations. Air Power Journal Spring: 53-58.
18. Crandall J E, McCarthy D M, Araki K Y, Sims J R, Ren J Q, Bhide P G (2007) Dopamine receptor activation modulates GABA neuron migration from the basal forebrain to the cerebral cortex. J Neurosci 27:3813-3822.
19. Dillon G M, Qu X, Marcus J N, Dodart J C (2008) Excitotoxic lesions restricted to the dorsal CA1 field of the hippocampus impair spatial memory and extinction learning in C57BL/6 mice. Neurobiol Learn Mem 90:426-433.
20. Dillon G M, Shelton D, McKinney A P, Caniga M, Marcus J N, Ferguson M T, Kornecook T J, Dodart J C (2009) Prefrontal cortex lesions and scopolamine impair attention performance of C57BL/6 mice in a novel 2-choice visual discrimination task. Behav Brain Res 204:67-76.
21. Eliyahu U, Berlin S, Hadad E, Heled Y, Moran D S (2007) Psychostimulants and military operations. Mil Med 172:383-387.
22. Gerasimov A A, Volkova A M (1991) [Treatment of patients with lumbar osteochondrosis by the method of intra-tissular electric stimulation]. Ortop Travmatol Protez: 13-17.

23. Gerasimov M R, Franceschi M, Volkow N D, Gifford A, Gatley S J, Marsteller D, Molina P E, Dewey S L (2000) Comparison between Intraperitoneal and Oral Methylphenidate Administration: A Microdialysis and Locomotor Activity Study. J Pharmacol Exp Ther 295:51-57.
24. Huijbregts S C, Warren A J, de Sonneville L M, Swaab-Barneveld H (2008) Hot and cool forms of inhibitory control and externalizing behavior in children of mothers who smoked during pregnancy: an exploratory study. J Abnorm Child Psychol 36:323-333.
25. Jasinski D R (2000) An evaluation of the abuse potential of modafinil using methylphenidate as a reference. J Psychopharmacol 14:53-60.
26. Jasinski D R, Henningfield J E (1989) Human abuse liability assessment by measurement of subjective and physiological effects. NIDA Res Monogr 92:73-100.
27. Jayaram-Lindstrom N, Wennberg P, Hurd Y L, Franck J (2004) Effects of naltrexone on the subjective response to amphetamine in healthy volunteers. J Clin Psychopharmacol 24:665-669.
28. Johanson C E, Schuster C R (1975) A choice procedure for drug reinforcers: cocaine and methylphenidate in the rhesus monkey. J Pharmacol Exp Ther 193:676-688.
29. Klein-Schwartz W (2002) Abuse and toxicity of methylphenidate. Curr Opin Pediatr 14:219-223.
30. Kollins S H, MacDonald E K, Rush C R (2001) Assessing the abuse potential of methylphenidate in non-human and human subjects: a review. Pharmacol Biochem Behav 68:611-627.
31. Kubrusly R C, Bhide P G (2010) Cocaine exposure modulates dopamine and adenosine signaling in the fetal brain. Neuropharmacology 58:436-443.
32. Kuczenski R, Segal D S (2001) Locomotor effects of acute and repeated threshold doses of amphetamine and methylphenidate: relative roles of dopamine and norepinephrine. J Pharmacol Exp Ther 296:876-883.
33. Kuczenski R, Segal D S (2002) Exposure of adolescent rats to oral methylphenidate: preferential effects on extracellular norepinephrine and absence of sensitization and cross-sensitization to methamphetamine. J Neurosci 22:7264-7271.
34. Kuczenski R, Segal D S (2005) Stimulant actions in rodents: implications for attention-deficit/hyperactivity disorder treatment and potential substance abuse. Biol Psychiatry 57:1391-1396.
35. Madras B K, Fahey M A, Bergman J, Canfield D R, Spealman R D (1989) Effects of cocaine and related drugs in nonhuman primates. I. [3H]cocaine binding sites in caudate-putamen. J Pharmacol Exp Ther 251:131-141.
36. Malanga C J, Ren J Q, Guerriero R M, Kosofsky B E (2009) Augmentation of cocaine-sensitized dopamine release in the nucleus accumbens of adult mice following prenatal cocaine exposure. Dev Neurosci 31:76-89.
37. Maldonado R, Saiardi A, Valverde O, Samad T A, Rogues B P, Borrelli E (1997) Absence of opiate rewarding effects in mice lacking dopamine D2 receptors. Nature 388:586-589.
38. McCabe S E, Teter C J, Boyd C J, Guthrie S K (2004) Prevalence and correlates of illicit methylphenidate use among 8th, 10th, and 12th grade students in the United States, 2001. J Adolesc Health 35:501-504.
39. Meririnne E, Kankaanpaa A, Seppala T (2001) Rewarding properties of methylphenidate: sensitization by prior exposure to the drug and effects of dopamine D1- and D2-receptor antagonists. J Pharmacol Exp Ther 298:539-550.
40. Nyholt D R (2004) A simple correction for multiple testing for single-nucleotide polymorphisms in linkage disequilibrium with each other. Am J Hum Genet 74:765-769.
41. Olfson M, Marcus S C, Weissman M M, Jensen P S (2002) National trends in the use of psychotropic medications by children. J Am Acad Child Adolesc Psychiatry 41:514-521.
42. Paine T A, Tomasiewicz H C, Zhang K, Carlezon W A, Jr. (2007) Sensitivity of the five-choice serial reaction time task to the effects of various psychotropic drugs in Sprague-Dawley rats. Biol Psychiatry 62:687-693.
43. Patrick K S, Markowitz J S (1997) Pharmacology of methylphenidate, amphetamine enantiomers and pemoline in attention-deficit hyperactivity disorder. Human Psychopharmacol 12:527-546.
44. Paxinos G, Franklin K B J (2001) The mouse brain in stereotaxic coordinates, 2nd Edition. San Diego, Calif., USA: Academic Press.
45. Popolo M, McCarthy D M, Bhide P G (2004) Influence of dopamine on precursor cell proliferation and differentiation in the embryonic mouse telencephalon. Dev Neurosci 26:229-244.
46. Robbins T W (2002) ADHD and addiction. Nat Med 8:24-25.
47. Safer D J, Zito J M, Fine E M (1996) Increased methylphenidate usage for attention deficit disorder in the 1990s. Pediatrics 98:1084-1088.
48. Sarhill N, Walsh D, Nelson K A, Homsi J, LeGrand S, Davis M P (2001) Methylphenidate for fatigue in advanced cancer: A prospective open-label pilot study. American Journal of Hospice and Palliative Medicine 18:187-192.
49. Seeman P, Madras B (2002) Methylphenidate elevates resting dopamine which lowers the impulse-triggered release of dopamine: a hypothesis. Behav Brain Res 130:79-83.
50. Sivam S P (1989) Cocaine selectively increases striatonigral dynorphin levels by a dopaminergic mechanism. J Pharmacol Exp Ther 250:818-824.
51. Soderman A R, Unterwald E M (2008) Cocaine reward and hyperactivity in the rat: sites of mu opioid receptor modulation. Neuroscience 154:1506-1516.
52. Spear L P (2000) The adolescent brain and age-related behavioral manifestations. Neurosci Biobehav Rev 24:417-463.
53. Spencer T J, Abikoff H B, Connor D F, Biederman J, Pliszka S R, Boellner S, Read S C, Pratt R (2006a) Efficacy and safety of mixed amphetamine salts extended release (adderall XR) in the management of oppositional defiant disorder with or without comorbid attention-deficit/hyperactivity disorder in school-aged children and adolescents: A 4-week, multicenter, randomized, double-blind, parallel-group, placebo-controlled, forced-dose-escalation study. Clin Ther 28:402-418.
54. Spencer T J, Biederman J, Ciccone P E, Madras B, Dougherty D D, Bonab A A, Livni E, Fischman A (2006b) Pharmacokinetics, Detection, Likeability and Dislikeability of Two Formulations of Long-Acting Oral Methylphenidate. In: 53nd Annual meeting of the American Academy of Child and Adolescent Psychiatry. San Diego, Calif., USA.
55. Spencer T J, Biederman J, Ciccone P E, Madras B K, Dougherty D D, Bonab A A, Livni E, Parasrampuria D A, Fischman A J (2006c) PET study examining pharmacokinetics, detection and likeability, and dopamine transporter receptor occupancy of short- and long-acting oral methylphenidate. Am J Psychiatry 163:387-395.
56. Teter C J, McCabe S E, Boyd C J, Guthrie S K (2003) Illicit methylphenidate use in an undergraduate student sample: prevalence and risk factors. Pharmacotherapy 23:609-617.
57. Tien L-T, Park Y, Fan L-W, Ma T, Loh H H, Ho I K (2003) Increased dopamine D2 receptor binding and enhanced apomorphine-induced locomotor activity in [mu]-opioid receptor knockout mice. Brain Research Bulletin 61:109-115.
58. Trigo J M, Martin-Garcia E, Berrendero F, Robledo P, Maldonado R (2009) The endogenous opioid system: A common substrate in drug addiction. Drug Alcohol Depend. Tzschentke T M (1998) Measuring reward with the conditioned place preference paradigm: a comprehensive review of drug effects, recent progress and new issues. Prog Neurobiol 56:613-672.
59. Volkow N D (2006) Stimulant medications: how to minimize their reinforcing effects? Am J Psychiatry 163: 359-361.
60. Volkow N D, Wang G J, Fowler J S, Ding Y S (2005) Imaging the effects of methylphenidate on brain dopamine: new model on its therapeutic actions for attention-deficit/hyperactivity disorder. Biol Psychiatry 57:1410-1415.
61. Xia Y-f, He L, Whistler J L, Hjelmstad G O (2007) Acute Amphetamine Exposure Selectively Desensitizes [kappa]-Opioid Receptors in the Nucleus Accumbens. Neuropsychopharmacology 33:892-900.
62. Zhu J, Luo L Y, Li J G, Chen C, Liu-Chen L Y (1997) Activation of the cloned human kappa opioid receptor by agonists enhances [35S]GTPgammaS binding to membranes: determination of potencies and efficacies of ligands. J Pharmacol Exp Ther 282:676-684.
63. Zito J M, Safer D J, dosReis S, Gardner J F, Boles M, Lynch F (2000) Trends in the prescribing of psychotropic medications to preschoolers. JAMA 283:1025-1030.
64. Zubieta J K, Gorelick D A, Stauffer R, Ravert H T, Dannals R F, Frost J J (1996) Increased mu opioid receptor binding detected by PET in cocaine-dependent men is associated with cocaine craving. Nat Med 2:1225-1229.
65. Zuvekas S H, Vitiello B, Norquist G S (2006) Recent trends in stimulant medication use among U.S. children. Am J Psychiatry 163:579-585.

What is claimed is:

1. A method to decrease the euphoria associated with the use of therapeutic doses of methylphenidate comprising administering to a subject a therapeutic amount of methylphenidate and administering to the subject a mu opioid receptor antagonist, wherein the subject is suffering from attention deficit hyperactivity disorder or narcolepsy that is treated by methylphenidate to thereby decrease euphoria associated with administration of methylphenidate and treat attention deficit hyperactivity disorder or narcolepsy in the subject.

2. The method of claim 1, wherein the subject is at risk for the development of euphoria.

3. The method of claim 1, wherein the mu opioid receptor antagonist is selected from the group consisting of naltrexone, naloxone, diprenorphine, etorphine, dihydroetorphine, levallorphan, nalomhine, naloxonazine, piperidine derivatives, cyprodime, β-funaltrexamine, nalbuphine, D-Phe-Cys-Tyr-D-Trp-Arg-Thr-Pen-Thr-$NH_2$ (CTAP), D-Tic-Cys-Tyr-D-Trp-Orn-Thr-Pen-Thr-$NH_2$ (TCTOP), D-Tic-Cys-Tyr-D-Trp-Arg-Thr-Pen-Thr-$NH_2$ (TCTAP), D-Phe-Cys-Tyr-D-Trp-Orn-Thr-Pen-Thr-$NH_2$ (CTOP), quadazocine, flumazenil, Tyr MIF-1, clocinnamox, naloxazone, dezocine, ciramadol, and combinations thereof.

4. The method of claim 1, wherein the administering is oral.

5. The method of claim 1, wherein methylphenidate and the mu opioid receptor antagonist are administered in the same pharmaceutical composition.

6. The method of claim 1, wherein methylphenidate and the mu opioid receptor antagonist are administered sequentially.

7. The method of claim 1, wherein the mu opioid receptor antagonist is administered in a dosage of from about 5 mg/kg to about 15 mg/kg.

8. The method of claim 1, wherein the mu opioid receptor antagonist is administered in a dosage of from about 5 mg/kilogram to about 10 mg/kilogram.

9. The method of claim 1, wherein about 0.5-1.0 mg of the mu opioid receptor antagonist is administered for every 0.75 mg of methylphenidate.

10. The method of claim 1, wherein about 1.0 mg of the mu opioid receptor antagonist is administered for every 0.75 mg of methylphenidate.

11. The method of claim 1, wherein about 5 mg of the mu opioid receptor antagonist is administered for every 6 mg of methylphenidate.

12. The method of claim 1, wherein about 10 mg of the mu opioid receptor antagonist is administered for every 6 mg of methylphenidate.

13. The method of claim 1, wherein the subject has narcolepsy.

14. The method of claim 1, wherein the mu opioid receptor antagonist is naltrexone.

15. The method of claim 1, wherein methylphenidate and mu opioid receptor antagonist are the sole pharmaceutical agents administered to the subject.

16. The method of claim 1, wherein the subject has attention deficit hyperactivity disorder.

17. The method of claim 1, wherein the subject is not addicted to methylphenidate.

* * * * *